US010786619B2

(12) United States Patent
Germain et al.

(10) Patent No.: US 10,786,619 B2
(45) Date of Patent: Sep. 29, 2020

(54) FLUID MANAGEMENT SYSTEM AND METHODS

(71) Applicant: BOSTON SCIENTIFIC SCIMED, INC., Maple Grove, MN (US)

(72) Inventors: Aaron Germain, Campbell, CA (US); Kyle Klein, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 205 days.

(21) Appl. No.: 15/913,223

(22) Filed: Mar. 6, 2018

(65) Prior Publication Data

US 2018/0193550 A1 Jul. 12, 2018

Related U.S. Application Data

(63) Continuation of application No. 14/168,248, filed on Jan. 30, 2014, now Pat. No. 9,943,639.
(Continued)

(51) Int. Cl.
*A61M 3/02* (2006.01)
*A61B 17/32* (2006.01)
(Continued)

(52) U.S. Cl.
CPC ..... *A61M 3/0229* (2013.01); *A61B 17/32002* (2013.01); *A61B 17/42* (2013.01);
(Continued)

(58) Field of Classification Search
CPC ........ A61M 3/0229; A61M 2210/1433; A61B 17/42; A61B 18/1485; A61B 2218/002
See application file for complete search history.

(56) References Cited

U.S. PATENT DOCUMENTS 4,092,246 A * 5/1978 Kummer ............... A61M 5/165
210/494.1
4,650,462 A 3/1987 DeSatnick et al.
(Continued)

FOREIGN PATENT DOCUMENTS

EP 0153190 A1 8/1985
EP 2100567 A1 9/2009
(Continued)

OTHER PUBLICATIONS

AAGL Practice Report: Practice Guidelines for the Management of Hysteroscopic Distending Media: (Replaces Hysteroscopic Fluid Monitoring Guidelines. J Am Assoc Gynecol Laparosc. 2000;7: 167-168) J Minim Invasive Gynecol. Mar.-Apr. 2013;20:137-48. doi: 10.1016/j.jmig.2012.12.002.
(Continued)

*Primary Examiner* — Bradley J Osinski
(74) *Attorney, Agent, or Firm* — Seager, Tufte & Wickhem, LLP

(57) ABSTRACT

A hysteroscopic fluid management system includes a saline source with an electrolyte concentration, at least one pressure mechanism for circulating saline to and from a targeted site and through a filter having filter characteristics back to the source, and a controller. The controller provides a saline inflow in a first flow path to the site and a saline outflow in a second flow path from the site through the filter and back to the source at a controlled flow rate. A diagnostic or therapeutic procedure is performed at the site in the presence of the saline. The filter characteristics and the controlled flow rate are selected to (1) cause substantially no change in the electrolyte concentration in the saline, (2) to prevent hemolysis of greater than 5% of filtered red blood cells exposed to the saline, and/or (3) to minimize effect on prothrombin time of plasma exposed to the filter.

20 Claims, 13 Drawing Sheets

Related U.S. Application Data

(60) Provisional application No. 61/896,489, filed on Oct. 28, 2013.

(51) Int. Cl.
  *A61B 17/42* (2006.01)
  *A61M 1/00* (2006.01)
  *A61B 18/00* (2006.01)
  *A61B 18/14* (2006.01)

(52) U.S. Cl.
  CPC .......... *A61M 1/006* (2014.02); *A61M 1/0058* (2013.01); *A61M 3/022* (2014.02); *A61M 3/0208* (2014.02); *A61M 3/0212* (2014.02); *A61B 18/1485* (2013.01); *A61B 2017/4216* (2013.01); *A61B 2018/00559* (2013.01); *A61B 2018/00577* (2013.01); *A61B 2018/00607* (2013.01); *A61B 2018/00982* (2013.01); *A61B 2217/005* (2013.01); *A61B 2217/007* (2013.01); *A61B 2218/002* (2013.01); *A61M 2202/0429* (2013.01); *A61M 2205/50* (2013.01); *A61M 2205/7545* (2013.01); *A61M 2210/1433* (2013.01)

(56) References Cited

U.S. PATENT DOCUMENTS

| | | |
|---|---|---|
| 4,735,603 A | 4/1988 | Goodson et al. |
| 4,971,034 A | 11/1990 | Doi et al. |
| 4,998,527 A | 3/1991 | Meyer |
| 5,098,375 A | 3/1992 | Baier |
| 5,106,364 A | 4/1992 | Hayafuji et al. |
| 5,169,397 A | 12/1992 | Sakashita et al. |
| 5,277,696 A | 1/1994 | Hagen |
| 5,312,399 A | 5/1994 | Hakky et al. |
| 5,320,091 A | 6/1994 | Grossi et al. |
| 5,382,229 A | 1/1995 | Grabenkort et al. |
| 5,437,629 A | 8/1995 | Goldrath |
| 5,456,689 A | 10/1995 | Kresch et al. |
| 5,456,835 A * | 10/1995 | Castino .............. B01D 39/1623 210/490 |
| 5,476,447 A | 12/1995 | Noda et al. |
| 5,527,331 A | 6/1996 | Kresch et al. |
| 5,643,203 A | 7/1997 | Beiser et al. |
| 5,669,921 A | 9/1997 | Berman et al. |
| 5,730,752 A | 3/1998 | Alden et al. |
| 5,779,662 A | 7/1998 | Berman |
| 5,810,858 A | 9/1998 | Berman et al. |
| 5,823,990 A | 10/1998 | Henley |
| 5,830,180 A | 11/1998 | Chandler et al. |
| 5,853,392 A | 12/1998 | Dennis |
| 5,906,615 A | 5/1999 | Thompson |
| 5,925,050 A | 7/1999 | Howard, III |
| 6,032,673 A | 3/2000 | Savage et al. |
| 6,039,748 A | 3/2000 | Savage |
| 6,109,268 A | 8/2000 | Thapliyal et al. |
| RE36,914 E | 10/2000 | Carlsen et al. |
| 6,206,014 B1 | 3/2001 | Cameron, III et al. |
| 6,245,084 B1 | 6/2001 | Mark et al. |
| 6,358,263 B2 | 3/2002 | Mark et al. |
| 6,629,986 B1 | 10/2003 | Ross et al. |
| 7,029,451 B2 | 4/2006 | Anderson et al. |
| 7,070,604 B1 | 7/2006 | Garito et al. |
| 7,204,821 B1 | 4/2007 | Clare et al. |
| 7,226,459 B2 | 6/2007 | Cesarini et al. |
| 7,384,417 B2 | 6/2008 | Cucin |
| 7,549,987 B2 | 6/2009 | Shadduck |
| 7,674,259 B2 | 3/2010 | Shadduck |
| 7,892,229 B2 | 2/2011 | Shadduck et al. |
| 8,061,359 B2 | 11/2011 | Emanuel |
| 8,313,485 B2 | 11/2012 | Shadduck |
| 8,512,326 B2 | 8/2013 | Shadduck et al. |
| 8,568,424 B2 | 10/2013 | Shugrue et al. |
| 8,574,253 B2 | 11/2013 | Gruber et al. |
| 8,728,066 B2 | 5/2014 | Shadduck et al. |
| 8,840,625 B2 | 9/2014 | Adams et al. |
| 8,840,626 B2 | 9/2014 | Adams et al. |
| 8,951,274 B2 | 2/2015 | Adams et al. |
| 9,072,431 B2 | 7/2015 | Adams et al. |
| 9,095,366 B2 | 8/2015 | Sullivan et al. |
| 2002/0010463 A1 | 1/2002 | Muller et al. |
| 2002/0072745 A1 | 6/2002 | Truckai et al. |
| 2003/0060862 A1 | 3/2003 | Goble et al. |
| 2004/0049217 A1 | 3/2004 | Ross et al. |
| 2004/0092980 A1 | 5/2004 | Cesarini et al. |
| 2004/0102770 A1 | 5/2004 | Goble |
| 2004/0167427 A1 | 8/2004 | Quick et al. |
| 2004/0167428 A1 | 8/2004 | Quick et al. |
| 2004/0267255 A1 | 12/2004 | Auge, II et al. |
| 2005/0096649 A1 | 5/2005 | Adams |
| 2005/0236329 A1 | 10/2005 | Brotherton et al. |
| 2006/0047185 A1 | 3/2006 | Shener et al. |
| 2006/0135955 A1 | 6/2006 | Shadduck |
| 2006/0224154 A1 | 10/2006 | Shadduck et al. |
| 2007/0016182 A1 | 1/2007 | Lipson et al. |
| 2007/0021713 A1 | 1/2007 | Kumar et al. |
| 2007/0036768 A1 | 2/2007 | Fraser et al. |
| 2007/0088275 A1 | 4/2007 | Stearns et al. |
| 2007/0244353 A1 | 10/2007 | Larsen |
| 2008/0039832 A1 | 2/2008 | Palanker et al. |
| 2008/0065060 A1 | 3/2008 | Ein-Gal |
| 2008/0071269 A1 | 3/2008 | Hilario et al. |
| 2008/0091061 A1 | 4/2008 | Kumar |
| 2008/0091071 A1 | 4/2008 | Kumar |
| 2008/0097468 A1 | 4/2008 | Adams et al. |
| 2008/0097471 A1 | 4/2008 | Adams et al. |
| 2008/0287893 A1 | 11/2008 | Ineson |
| 2009/0069796 A1* | 3/2009 | Oskin .................... A61B 18/04 606/27 |
| 2009/0082715 A1 | 3/2009 | Charles |
| 2009/0137943 A1 | 5/2009 | Stearns et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2009/0312753 A1 | 12/2009 | Shadduck |
| 2010/0100091 A1 | 4/2010 | Truckai |
| 2010/0152533 A1 | 6/2010 | Mark |
| 2011/0031191 A1 | 2/2011 | Fukuda et al. |
| 2011/0150961 A1 | 6/2011 | Perry et al. |
| 2011/0224486 A1 | 9/2011 | Nguyen et al. |
| 2011/0264090 A1 | 10/2011 | Shadduck et al. |
| 2011/0306968 A1 | 12/2011 | Beckman et al. |
| 2012/0010464 A1 | 1/2012 | Adams et al. |
| 2012/0053583 A1 | 3/2012 | Palanker et al. |
| 2012/0172888 A1 | 7/2012 | Shugrue et al. |
| 2012/0172889 A1 | 7/2012 | Chin et al. |
| 2012/0271300 A9 | 10/2012 | Shadduck et al. |
| 2012/0330292 A1 | 12/2012 | Shadduck et al. |
| 2013/0046304 A1 | 2/2013 | Germain et al. |
| 2013/0079702 A1 | 3/2013 | Klein et al. |
| 2013/0103021 A1 | 4/2013 | Germain et al. |
| 2013/0172805 A1 | 7/2013 | Truckai et al. |
| 2013/0172870 A1 | 7/2013 | Germain et al. |
| 2013/0231652 A1 | 9/2013 | Germain et al. |
| 2013/0296847 A1 | 11/2013 | Germain et al. |
| 2014/0303551 A1 | 10/2014 | Germain et al. |
| 2014/0324065 A1 | 10/2014 | Bek et al. |
| 2015/0119795 A1 | 4/2015 | Germain et al. |

FOREIGN PATENT DOCUMENTS

| | | |
|---|---|---|
| GB | 2327351 A | 1/1999 |
| JP | 1989087708 A | 6/1989 |
| JP | 2000217908 A | 8/2000 |
| JP | 2007014854 A | 1/2007 |
| JP | 2008511397 A | 4/2008 |
| JP | 2011212450 A | 10/2011 |
| WO | 2005037088 A2 | 4/2005 |
| WO | 2009128435 A1 | 10/2009 |
| WO | 2010096139 A2 | 8/2010 |

(56) References Cited

FOREIGN PATENT DOCUMENTS

| WO | 2011060189 A1 | 5/2011 |
| WO | 2010096139 A3 | 12/2011 |
| WO | WO2014168985 A1 | 10/2014 |

OTHER PUBLICATIONS

Liu, et al. Clinical application of hysteriscopic electroresection in 775 cases. Di YHi Jun Yi Da Xue Xue Bao. Apr. 2004;24(4):467-9. (in Chinese with English abstract).

Phillips, et al. The Effect of Dilute Vasopressin Solution on Blood Loss During Operative Hysteroscopy. J Am Assoc Gynecol Laparosc. Aug. 1996;3(4, Supplement):S38.

International Search Report and Written Opinion dated Sep. 24, 2012 for PCT/US2012/043892.

International Search Report and Written Opinion dated Oct. 2, 2012 for PCT/US2012/045428.

International Search Report and Written Opinion dated Oct. 16, 2012 for PCT/US2012/044609.

International Search Report and Written Opinion dated Dec. 4, 2012 for PCT/US2012/056936.

\* cited by examiner

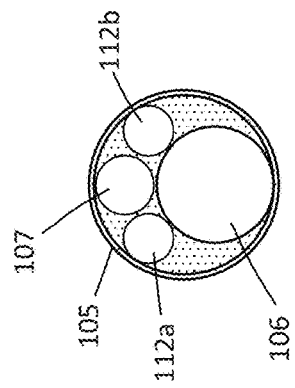
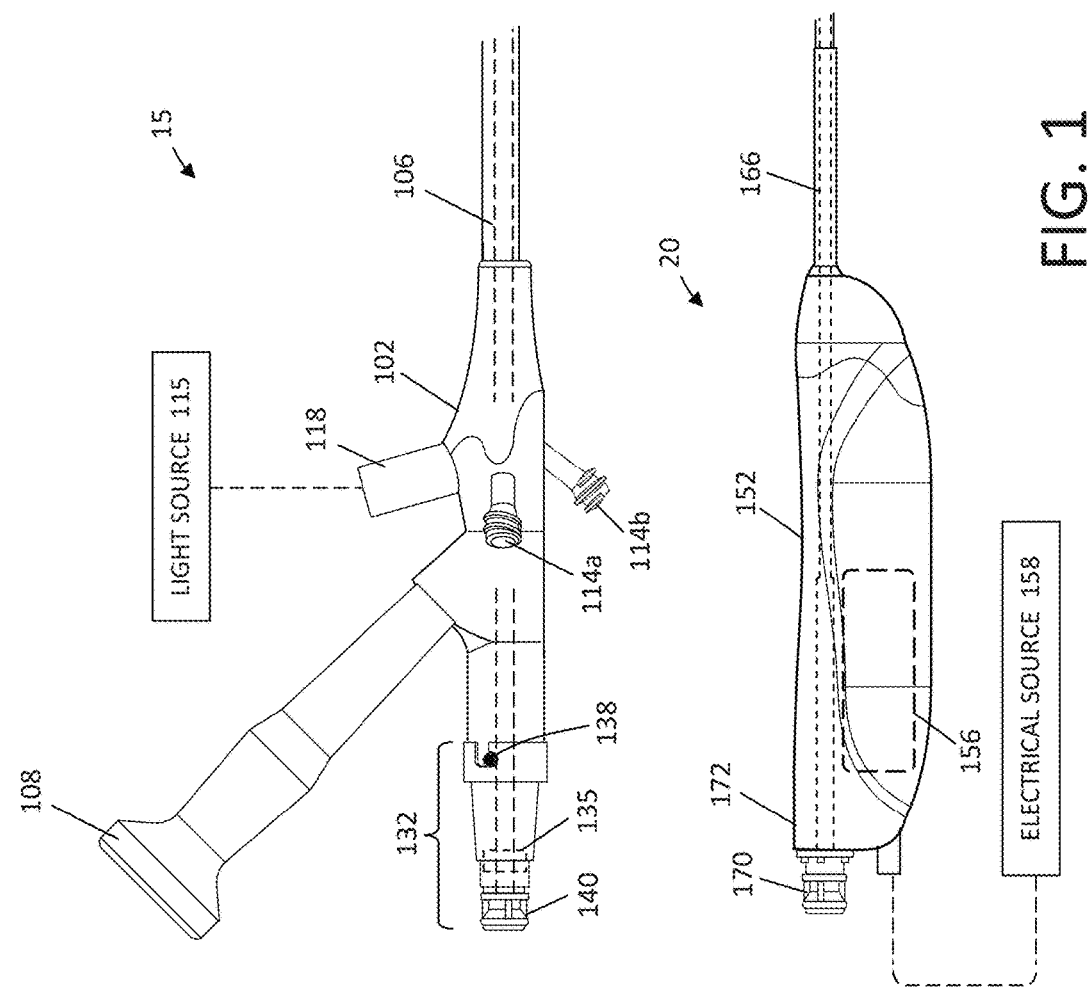
FIG. 2
FIG. 1

FLUID MANAGEMENT SYSTEM AND METHODS

CROSS-REFERENCE TO RELATED APPLICATIONS

This application is a continuation of U.S. application Ser. No. 14/168,248, filed Jan. 30, 2014, which claims the benefit of U.S. Provisional Application No. 61/896,489, filed Oct. 28, 2013, the full disclosures of which are incorporated herein by reference.

FIELD OF THE INVENTION

The present invention relates to fluid management systems and methods for use in diagnostic and operative hysteroscopic procedures, for example, for use in resecting and extracting uterine fibroid tissue, polyps and other abnormal uterine tissue.

BACKGROUND OF THE INVENTION

Uterine fibroids are non-cancerous tumors that develop in the wall of uterus. Such fibroids occur in a large percentage of the female population with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a resecting instrument through a working channel in the hysteroscope. The resecting instrument may be a mechanical tissue cutter or an electrosurgical resection device such as an RF loop. Mechanical cutting devices are disclosed in U.S. Pat. Nos. 7,226,459; 6,032,673; 5,730,752; and U.S. Published Patent Appl. 2009/0270898. An electrosurgical resecting device is disclosed in U.S. Pat. No. 5,906,615.

In a myomectomy or hysteroscopic resection, the initial step of the procedure includes distention of the uterine cavity to create a working space for assisting viewing through the hysteroscope. In a relaxed state, the uterine cavity collapses with the uterine walls in contact with one another. A fluid management system is used to distend the uterus to provide a working space by means of a fluid being introduced through a passageway in the hysteroscope under sufficient pressure to expand or distend the uterine cavity. The fluid management system can be used for diagnostic or operative hysteroscopic procedures. Typically, saline solution is used to as a distention fluid. Fluid management systems typically use a controller which controls inflows and outflows of distention fluid to maintain a set pressure in the uterine cavity. The distention fluid pressure provides a benefit in the tamponade effect on vascularized tissue at the resection site. The distention fluid pressure typically exceeds the patient's mean arterial pressure, and thus the pressure can prevent leakage of arterial blood from the resection site into the uterine cavity. When such arterial blood leaks into the distention fluid, it can reduce the clarity of the visual field and make the procedure more difficult or cause suspension of the procedure. Thus, it is useful to maintain fluid pressure above the arterial pressure to provide a clear visual field.

One disadvantage of the use of distention fluids in hysteroscopic procedures is that it places women at risk for fluid overload from intravasation of distention fluid by the patient's venous system. Such intravasation can cause electrolyte imbalances with a potential for pulmonary edema and congestive heart failure. A typical fluid management system has fluid deficit monitoring capabilities wherein the volume of intravasated fluid is determined by calculating the difference between the fluid weight/volume introduced into the patient minus the weight/volume of fluid collected from the patient during the course of a procedure. A typical fluid management system includes a visual display of fluid deficit and a warning signal for an excessive fluid deficit.

There are several disadvantages related to the use of conventional weight-based fluid management systems. First, it is typically difficult to maintain a pre-set fluid pressure to distend the uterine cavity during a resection procedure because the cutting device suctions fluid through the device to draw tissue into a cutting window and thereafter suctions fluid and resected tissue through the device to collection reservoirs. Thus, suctioning fluid from the uterine cavity needs to be compensated for with corresponding fluid inflows into the cavity to maintain cavity distention. Typical weight-based fluid management systems have a pressure sensor that will activate the inflow pump to deliver distention fluid to the uterine cavity when intra-cavity pressure drops. However, use of the cutting device and associated suction may cause a very rapid drop in pressure resulting in collapse of the cavity before replacement inflows of distention fluid are sufficient to maintain distention of the cavity. A collapse of the cavity results in loss of visualization and would require the physician to interrupt the procedure. The drop in intra-cavity distention fluid pressure also may result in leakage of greater amounts of blood into the cavity which further causes a loss of visualization.

One promising approach for fluid management in hysteroscopic and other endoscopic procedures is the recirculation and filtration of the saline electrolytic distention fluid. In order for such a saline filtration and recirculation system to be safe and effective, the filter and flow control system would need to provide a filtrate that does not include lysed red blood cells and that has an unaltered electrolyte concentration. Further, the filtrate should not cause any effect on a coagulation pathway of a patient or cause activation of an inflammation-related immune response in the patient. For these reasons, it would be desirable to provide filtering systems and methods and flow control systems for preventing hemolysis and for controlling electrolyte fluid management in hysteroscopic and other procedures which maintain the electrolytic concentrations in the saline and provide a filtrate that does not activate a coagulation response or an immune response in the event of intravasation of the filtrate. At least some of these objectives will be met by the inventions described below.

SUMMARY OF THE INVENTION

In a first aspect of the present invention, a recirculating fluid management system for use in hysteroscopic and other endoscopic procedures is provided, together with methods of operation wherein the system parameters are designed to substantially prevent hemolysis of filtered red blood cells. The fluid management system includes a saline source, an inflow pump, an outflow pump, and a controller operated by controller algorithms. The controller algorithms actuate the inflow pump to provide a saline inflow through a hysteroscope at an inflow rate into a uterine cavity or other site and actuates the outflow pump to provide a saline outflow through the endoscope at an outflow rate from the uterine cavity or other site and through a filter having selected filter characteristics and back to the saline source. A diagnostic or therapeutic procedure is performed in the uterine cavity or other site in the presence of saline, and the filter characteristics and a controlled outflow rate are selected to substantially prevent hemolysis of filtered red blood cells.

Hemolysis is the term for the rupture or lysis of red blood cells. Ruptured red blood cells in circulation may produce increased levels of free plasma hemoglobin capable of inducing toxic effects in the kidney or other organs. Lysed red blood cell also could affect the electrolyte concentration of the filtrate. In a filtration system, hemolysis can be caused at the interface of the filter membrane by excessive pressure or flow rates in combination with inadequate filter capacity, oversized pores of the filter and/or uncontrolled back pressure on the filter which can affect the pressure gradient across the filter membrane. For this reason, the selection of filter parameters and flow parameters are critical for insuring that hemolysis is prevented or limited.

The molecular filter of the present invention has specific characteristics selected to cooperate with flow parameters to prevent hemolysis and to achieve other particular outcomes as discussed below. The filter may comprise hollow fibers with a total lumen surface area of at least 0.5 $m^2$ and may have a filtration capacity of at least 40 ml of blood, preferably at least 60 ml of blood and more preferably at least 80 ml of blood. The lumens of the hollow fibers will typically have a diameter of less than 400 microns, more typically less than 300 microns, and often less than 200 microns. In specific instances, the hollow fibers have a nominal molecular weight limit (NMWL) of 50 kDa or less or 20 kDa or less. In specific embodiments, the controller may be programmed to cause the outflow pump to limit pressure at the filter interface to a maximum of 100 psi, more typically less than 50 psi. The filter further has a capacity of flow through the filter membrane of at least 500 ml/min. The back pressure caused by the height of the saline source above the filter is 3 psi or less. In a specific embodiment, the controller may be programmed to cause the inflow and outflow pumps to maintain a set pressure in the uterine cavity. The filter characteristics and controlled outflow rate through the filter may be selected to prevent hemolysis of greater than 5% of filtered red blood cells.

The filter characteristics and controlled outflow rate may be still further selected to prevent any effect on a coagulation pathway of a patient in a potential intravasation of filtrate as shown by a Prothrombin Time (PT) assay or an Unactivated Partial Thromboplastic Time assay (UPTT).

In a second aspect of the present invention, a method of fluid management in hysteroscopic or other endoscopic procedures comprises providing a fluid management system including a saline source having an electrolyte concentration, an inflow pump, an outflow pump and a controller operated by control algorithms. The control algorithms actuate the inflow pump to provide a saline inflow at an inflow rate into a uterine cavity or other site and actuate the outflow pump to provide a saline outflow at an outflow rate from the uterine cavity or other site through a filter having filter characteristics and back to the saline source. The filter characteristics and the controlled outflow rate are selected to cause substantially no change in the electrolyte concentration in the saline passing through the filter. A diagnostic or therapeutic procedure is performed at the site in the presence of saline.

In specific embodiments of the second aspect, the controller may be programmed to cause the inflow and outflow pumps to maintain a set pressure in the site. The controller may also be programmed to cause the pumps to limit pressure at the filter to a maximum of 50 psi.

The filter of the second aspect of the present invention will also have specific characteristics selected to achieve particular outcomes as discussed below. The filter may comprise hollow fibers with a total lumen surface area of at least 0.5 $m^2$ and may have a filtration capacity of at least 40 ml of blood, preferably at least 60 ml of blood and more preferably at least 80 ml of blood. The lumens of the hollow fibers will typically have a diameter of less than 400 microns, more typically less than 300 microns, and often less than 200 microns. In specific instances, the hollow fibers have a nominal molecular weight limit (NMWL) of 50 kDa or less or 20 kDa or less.

The controller and inflow and outflow pumps of the second aspect of the present invention are typically capable of providing the saline inflow and outflow at rates ranging from 0 ml/min to at least 500 ml/min. The filter characteristics and controlled outflow rate may be further selected to cause substantially no change in the electrolyte concentration in the saline passing through the filter. The filter characteristics and controlled outflow rate may be still further selected to prevent any effect on a coagulation pathway of a patient in the event of intravasation of filtrate as shown by a Prothrombin Time (PT) assay or an Unactivated Partial Thromboplastic Time assay (UPTT).

In a third aspect of the present invention, a re-circulating fluid management system is provided which includes a saline source, a pump system for providing fluid inflow and outflows, a controller and control algorithms, and a filter system having selected characteristics for filtering the outflows that return to the source. A method includes circulating a distention fluid from the source in an inflow to a treatment site and an outflow from the site through a filter resulting in a flow of a filtrate back to the source, wherein the circulating step includes filtering the outflow under filtering parameters that provide a filtrate that causes no substantial effect on an extrinsic or intrinsic coagulation pathway as verified by Prothrombin Time and Unactivated Partial Thromboplastic Time assays. Thereafter, a diagnostic or therapeutic procedure is performed in the site.

In specific embodiments of the third aspect, the controller may be programmed to cause the inflow and outflow pumps to maintain a set pressure in the site. The controller may also be programmed to cause the pumps to limit pressure at the filter to a maximum of 30 psi. The controller may further be programmed to cause the pumps to limit pressure at the filter to a maximum of 50 psi or 100 psi.

The filter of the third aspect of the present invention will also have specific characteristics selected to achieve particular outcomes as discussed below. The filter may comprise hollow fibers with a total lumen surface area of at least 0.5 $m^2$ and may have a filtration capacity of at least 40 ml of blood, preferably at least 60 ml of blood more preferably at least 80 ml of blood. The lumens of the hollow fibers will typically have a diameter of less than 400 microns, more typically less than 300 microns, and often less than 200 microns. In specific instances, the hollow fibers have a nominal molecular weight limit (NMWL) of 50 kDa or less or 20 kDa or less.

The controller and inflow and outflow pumps of the third aspect of the present invention are typically capable of providing the saline inflow and outflow at rates ranging from 0 ml/min to at least 500 ml/min. The filter characteristics and controlled outflow rate through the filter may be further selected to cause substantially no change in the electrolyte concentration in the saline passing through the filter. The filter characteristics and controlled flow rates may be still further selected to substantially prevent hemolysis of filtered red blood cells.

In a fifth aspect of the invention, a re-circulating fluid management system is provided which includes a saline source, a pump system for providing fluid inflow and outflows, a controller and control algorithms, and a filter system having selected characteristics for filtering the outflows that return to the source. The filter characteristics are selected to cooperate with selected control algorithms to provide a maximum flow rate and pressure at the filter interface. The selected filter characteristics and maximum flow parameters have no substantial effect on an immune system pathway as verified by a Complement Activation assay looking at C3a or C5b concentrations.

In a sixth aspect of the invention, a re-circulating fluid management system is provided which includes a saline source, a pump system for providing fluid inflow and outflows, a controller and control algorithms, and a filter system having selected characteristics for filtering the outflows that return to the source. The filter characteristics are selected to cooperate with selected control algorithms to provide a maximum flow rate and pressure at the filter interface. The selected filter characteristics and maximum flow parameters have no effect on platelet activation as verified by a Platelet Aggregation assay.

BRIEF DESCRIPTION OF DRAWINGS

FIG. 1 is a view of an endoscope and a tissue resecting device configured for insertion through the working channel of the endoscope.

FIG. 2 is a cross section of the shaft portion of the endoscope of FIG. 1 taken along line 2-2 of FIG. 1.

DETAILED DESCRIPTION OF THE INVENTION

Figure 3:
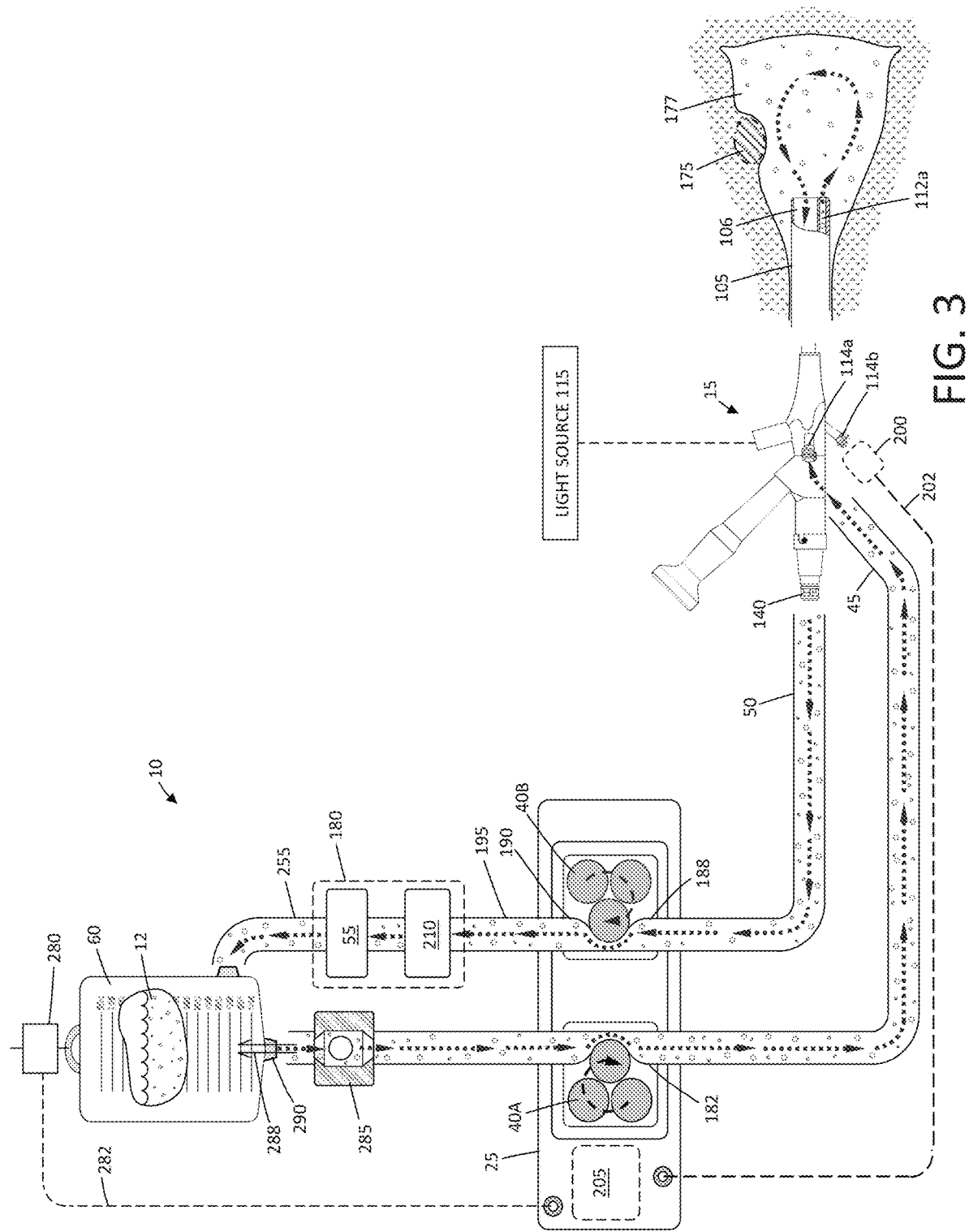
FIG. 3 is a schematic view of a fluid management system of the invention that re-circulates saline distention fluid illustrated in conjunction with an endoscope and being used in a diagnostic hysteroscopic procedure.

FIGS. 1-5 illustrate various components of a hysteroscopic system for performing a myomectomy or fibroid removal procedure. The myomectomy system integrates a re-circulating fluid management system 10 corresponding to the invention together with a known type of endoscope 15 and a motor driven resecting device 20.

More in particular, the fluid management system 10 is adapted to use saline solution 12 as a distention fluid to distend the uterine cavity and uses a controller 25 and first and second positive displacement pumps (40A and 40B) to re-circulate saline solution through an inflow line 45, outflow line 50 and molecular filter 55 back to a saline source 60. The controller 25 optionally can be adapted to control various operations of the motor driven resection device 20, such as on-off modulation, the speed of rotational and/or reciprocation of a cutting element, and activation of one or more electrodes or another energy emitter for resection or coagulation. Further, the fluid management system 10 can make use of a dedicated channels in the endoscope 15 for fluid inflows, fluid outflows and pressure sensing. Since the system components (fluid management system 10, endoscope 15 and resecting device 20) are optionally integrated, this disclosure will initially describe embodiments of an endoscope 15 and exemplary resecting device 20 which then will allow for description of the fluid management system 10 corresponding to the invention and its methods of operation.

In general, the filtering system must use a molecular filter 55 that can effectively provide a sterile filtrate (i.e., the saline media after passing through the molecular filter) to thereafter re-circulate back to the fluid source 60. A molecular filter 55 can remove blood and tissue components, etc. down to a size of much less than 100 kDa, but such a filter will still permit electrolytes (e.g., salt) to pass through the filter membrane.

In order to develop the re-circulating fluid management system 10, a number of functional requirements were identified which led to the testing and ultimately the design of the molecular filter 55, flow control systems and controller algorithms that would achieve various objectives. It was determined that beyond the requirement of effective sterility of the filtrate, the filter 55, the controller 25, the pump system and controller algorithms would need to have design characteristics that would meet several other more specific parameters and perform in accordance with specific functional requirements which are described next.

It was determined that one requirement was that all red blood cells be removed from the filtrate to thus provide re-circulated saline that allows for the same visualization quality as normal saline from a new saline bag. Further, it was determined that the filter and flow parameters in a myomectomy procedure could not cause any unwanted reduction in filtration capacity after filtering an expected amount of blood and tissue components from the saline outflows in the fibroid removal procedure.

It was determined that another requirement was that the molecular filter and flow parameters would not alter the electrolyte concentration of the saline passing through the filter. A change in electrolyte concentration could pose a danger to the patient.

It was determined that a further requirement was that the molecular filter and flow parameters would not permit coagulation related factors to pass through the filter during the course of filtration that in turn could have an effect on a coagulation pathway of the patient in the event of a later intravasation of the re-circulated fluid.

It was determined that a further requirement was that the filter and flow parameters would not cause hemolysis, the rupture or lysis of red blood cells, within the fluid outflow. The presence of hemolytic material in a potential later intravasation could damage circulating red blood cells or could produce increased levels of free plasma hemoglobin that might cause unwanted effects on kidney function.

It was determined that another requirement was that the filter and flow parameters would not permit inflammation-related factors to pass through the filter which could potentially activate an inflammation pathway of the patient in the event of later intravasation of such factors.

Figure 4:
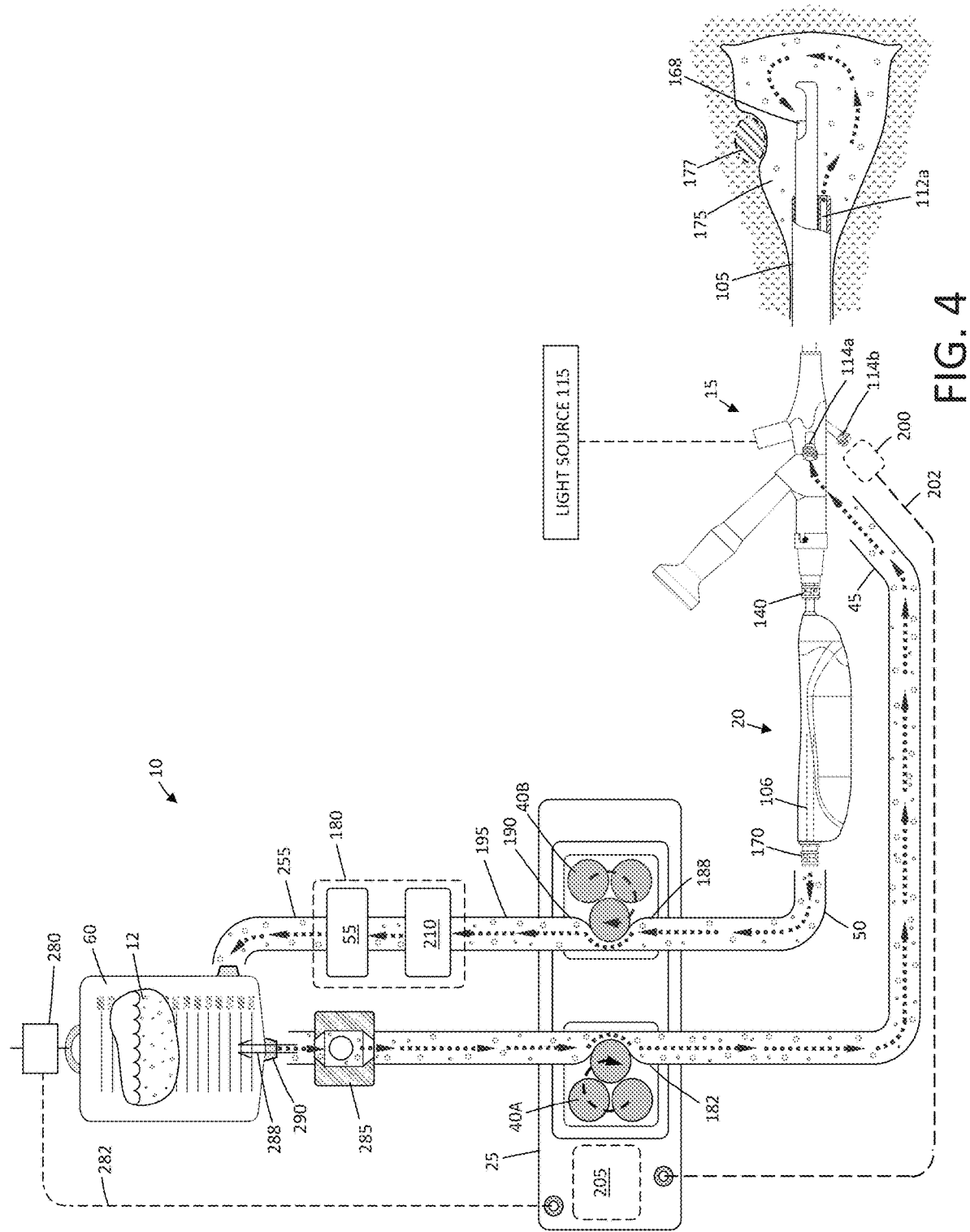
FIG. 4 is a schematic view of the fluid management system of FIG. 3 illustrated in conjunction with an endoscope and a motor driven resecting device and being used in a hysteroscopic myomectomy procedure.
Figure 5:
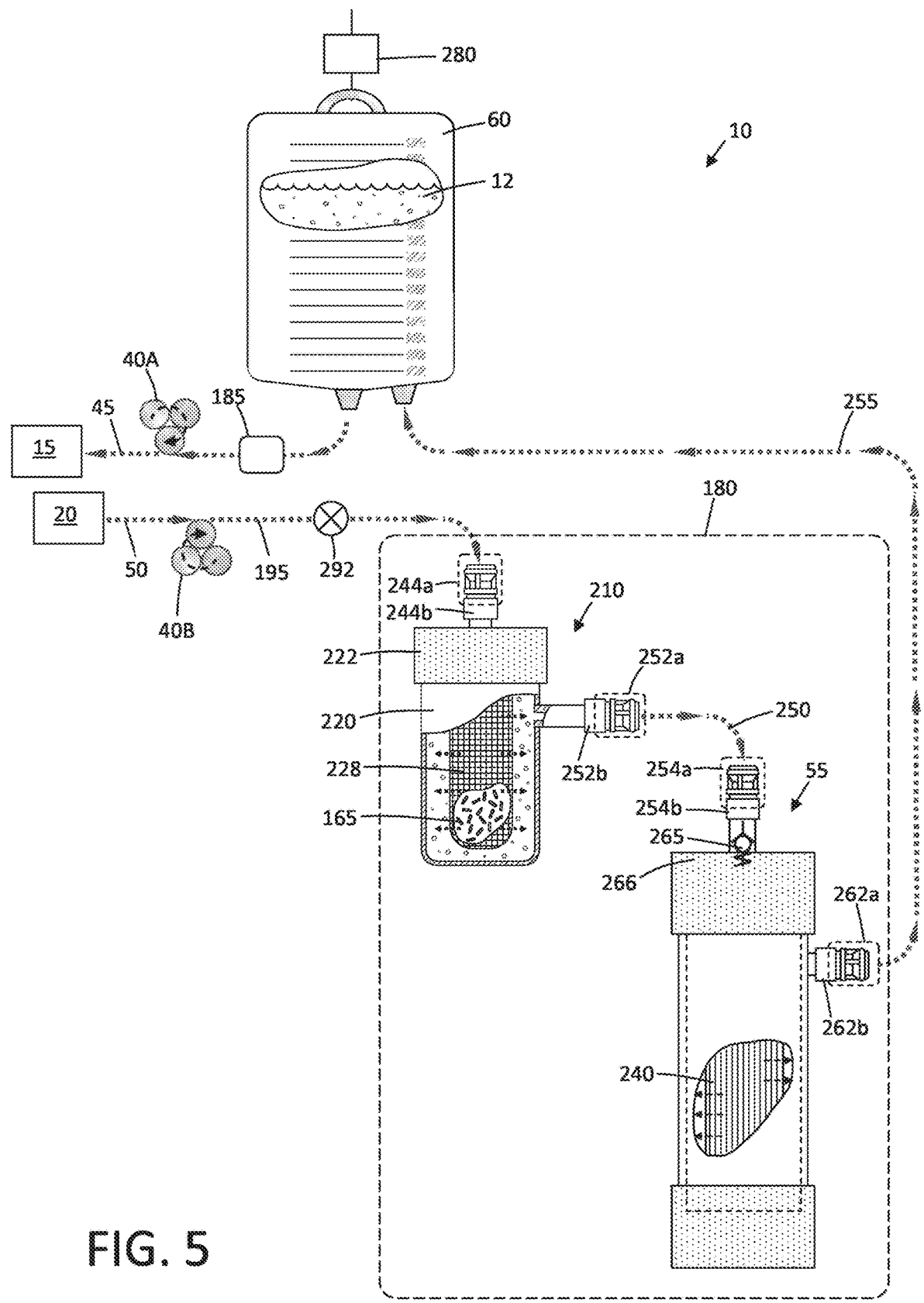
FIG. 5 is a cut-away schematic view of a filter module of the fluid management system of FIGS. 3-4.

Before describing the special characteristics of the molecular filter 55 and the controlled flow parameters of the fluid management system 10, the other components of an integrated system are described, i.e., the endoscope 15 and the resecting device 20. FIGS. 1-2 illustrate an endoscope 15 (or hysteroscope) and a tissue resecting device 20 that can be used in combination with the fluid management system 10 as shown in FIGS. 3-5 to perform an operative hysteroscopic procedure, for example to resect and extract abnormal tissue from a uterine cavity. The endoscope 15 also can be used with the fluid management system 10 of FIGS. 3-5 to perform a diagnostic hysteroscopy as will be described below.

In FIG. 1, the endoscope 15 has a handle 102 coupled to an elongated shaft 105 having a diameter of 3 mm to 10 mm. The working channel 106 therein may be round, D-shaped or any other suitable shape. In a variation shown in FIGS. 1-2, the working channel has a round configuration. The endoscope shaft 105 further carries an optics channel 107 cooperating with eyepiece 108 that can be coupled to a videoscopic camera as is known in the art. The endoscope shaft 105 further include one or more fluid inflow/outflow channels 112a, 112b that extend to connectors 114a, 114b and are configured for coupling to a fluid source 60 and optionally to a pressure sensor as will be described below (see FIGS. 3-4). In an embodiment, the endoscope shaft 105 has an axial length of 18 to 25 cm, and can comprise a 0° endoscope, or a 15° to 30° endoscope. A light source 115 can be coupled to light coupler 118 on the handle 102 of the endoscope 15.

FIG. 1 further illustrates a disposable adapter or seal housing 132 that carries one or more flexible seals 135 for sealing the shaft of the tissue resecting device 20 when introduced through the working channel 106 to prevent distention fluid from escaping from the uterine cavity. In one variation, the seal housing 132 is plastic and has a J-lock 138 for coupling to the endoscope handle 102. A quick-connect fitting 140 is provided at the proximal end of the seal housing that is adapted for connection to an outflow line 50 for use in diagnostic hysteroscopy as further described below.

Still referring to FIG. 1, the tissue resecting device 20 has a highly elongated shaft assembly 150 configured to extend through the working channel 106 in the endoscope 15. A handle 152 of the tissue resecting device 20 is adapted for manipulating the working end 155 of the device both rotationally and axially, for example, to orient the working end 155 to resect targeted fibroid tissue (see FIG. 4). In one variation, the tissue resecting device 20 is driven by electrical motor 156 coupled to electrical source 158, and the motor driven tool can be any type known in the art which reciprocates and/or rotates to cut, resect, abrade, grind or ablate tissue. As examples, the resecting device may be an RF resecting device as disclosed in U.S. Pat. No. 8,512,326 or a mechanical sharp-bladed cutter, for example, of the type described in U.S. Patent Application 20090270897 and U.S. Pat. No. 7,226,459.

In the prior art, the resecting device 20 typically resects tissue received within a window 160 in the working end 155. Thereafter, a negative pressure source assists in extracting fluid and tissue chips 165 through an extraction lumen 166 extending through an inner cutting sleeve 168 of the resecting device. In one variation shown in FIG. 1, the negative pressure source is operatively coupled to a quick-connect fitting 170 at the proximal end 172 of handle 152 of the resecting device 20.

FIGS. 3-4 illustrate a fluid management system 10 that is used in hysteroscopy in conjunction with endoscope 15 and resecting device 20 of FIGS. 1-2. In FIG. 3, the fluid management system 10 is first depicted schematically in a diagnostic hysteroscopic procedure, for example, for viewing and assessing the uterine cavity 175 and evaluating a fibroid 177 prior to a commencing a resection procedure. Referring to FIG. 3, in general, the fluid management system 10 comprises a fluid source or reservoir 60 containing a saline distention fluid 12. The controller 25 and two positive displacement (peristaltic) pumps (first infusion pump 40A, second outflow pump 40B) provide fluid inflows and outflows adapted to maintain distension of the uterine cavity. A filter system 180 is provided for filtering distention fluid 12 that is removed from the uterine cavity 210 and thereafter returned to the fluid source 60. The use of a recovered and filtered saline distention fluid 12 and the replenishment of the volume in fluid source 60 is advantageous because (i) the closed-loop system can effectively measure fluid deficit during a procedure and can provide fluid deficit warnings to insure patient safety; (ii) the closed-loop system can use only a single bag of saline having a useable volume of 2500 ml and provide a system lock-out to terminate a procedure after use of 2500 ml (or less) to thereby insure no more than 2500 ml intravasation, (iii) the system can reduce procedure cost by reducing the cost of saline bags and fluid disposal costs; (iv) the system can be set up and operated in a very time-efficient manner, and (v) the system can be compact and less expensive than current systems which will assist in enabling office-based diagnostic and therapeutic procedures. The 2500 ml limit of saline capacity was selected by the authors since this intravasation limit is aligned with practice guidelines established by the American Association of Gynecologic Laparoscopists (AAGL) (see, e.g., AAGL Practice Report: Practice Guidelines for the Management of Hysteroscopic Distending Media: (Replaces Hysteroscopic Fluid Monitoring Guidelines. J Am Assoc Gynecol Laparosc. 2000; 7:167-168), AAGL Advancing Minimally Invasive Gynecology Worldwide, Munro M G, et al., *J Min Invasive Gynecol.* 2013 March-April; 20(2):137-48).

The fluid management system 10 (FIGS. 3-4) includes a computer controller 25 that can be independent of a motor-driven resection device 20 or the controller 25 can be configured to operate both the fluid management system 10 and the motor-driven resection device 20. The controller 25 is adapted to control first and second peristaltic pumps 40A and 40B for providing inflows and outflows of a saline distention fluid 12 from source 60 for the purpose of distending the uterine cavity and controlling the intra-cavity pressure during either a diagnostic procedure (FIG. 3) or a resection procedure as depicted in FIG. 4.

In one variation shown in FIG. 3, the controller 25 controls peristaltic pump 40A to provide positive pressure at the outflow side 182 of the pump (FIG. 3) to provide inflows of distention fluid 12 through first flow line or inflow line 45 which is in communication with luer fitting 114a and fluid flow channel 112a in endoscope 15. The controller 25 further controls the second peristaltic pump 40B to provide negative pressure at the inflow side 188 of the pump (FIG. 3) to the second flow line or outflow line 50 to assist in providing outflows of distention fluid 12 from the uterine cavity 175. In operation, the second peristaltic pump 40B also operates to provide positive pressure on the outflow side 190 of pump 40B in the second outflow line portion 195 to pump outflows of the saline 12 through the filter system 180 and back to the fluid source 60.

In one system variation, the controller 25 has control algorithms that operate to control pressure in the uterine cavity 175 by pressure signals from a disposable pressure sensor 200 that is coupled to a fitting 114b in endoscope 15 which communicates with a flow channel 112b (see FIGS. 2 and 3) that extends through the endoscope shaft 105 to the uterine cavity. The pressure sensor 200 is operatively coupled to controller 25 by cable 202 which sends pressure signals to the controller 25. In one embodiment, the flow channel 112b has a diameter larger enough to allow highly accurate sensing of actual intra-cavity pressure. In prior art commercially-available fluid management systems, the intra-cavity pressure is typically estimated by various calculations using known flow rates through a pump or remote pressure sensors in the fluid inflow line and/or outflow lines that sometimes rely on back pressure calculations. Such prior art fluid management systems are stand-alone systems that are adapted for use with a variety of hysteroscopes. Most such systems are not able to use a pressure sensor that measures actual intra-cavity pressure. Thus, the prior art fluid management systems rely on algorithms and calculations to estimate intra-cavity pressure, which are typically not accurate.

The fluid channel or sensor channel 112b in communication with the pressure sensor 200 is independent of flow channel 112a used for inflows of saline into the uterine cavity 175. In the absence of fluid flows in channel 112b, the fluid in the channel 112b then forms a static column of fluid (air or liquid) that transmits changes in pressure to the sensor 200 as the pressure in the uterine cavity changes. In one variation, the sensor channel 112b has a cross-section of at least 1 mm, and fluid pressure within the pressure channel column is equivalent to the pressure in the uterine cavity. Thus, the pressure sensor 200 is capable of a direct measurement of pressure within the uterine cavity or other body cavity. In one method, the sensor channel 112b can be purged of air by opening a valve (not shown) to release air from the channel 112b and the sensor 200.

Figure 7:
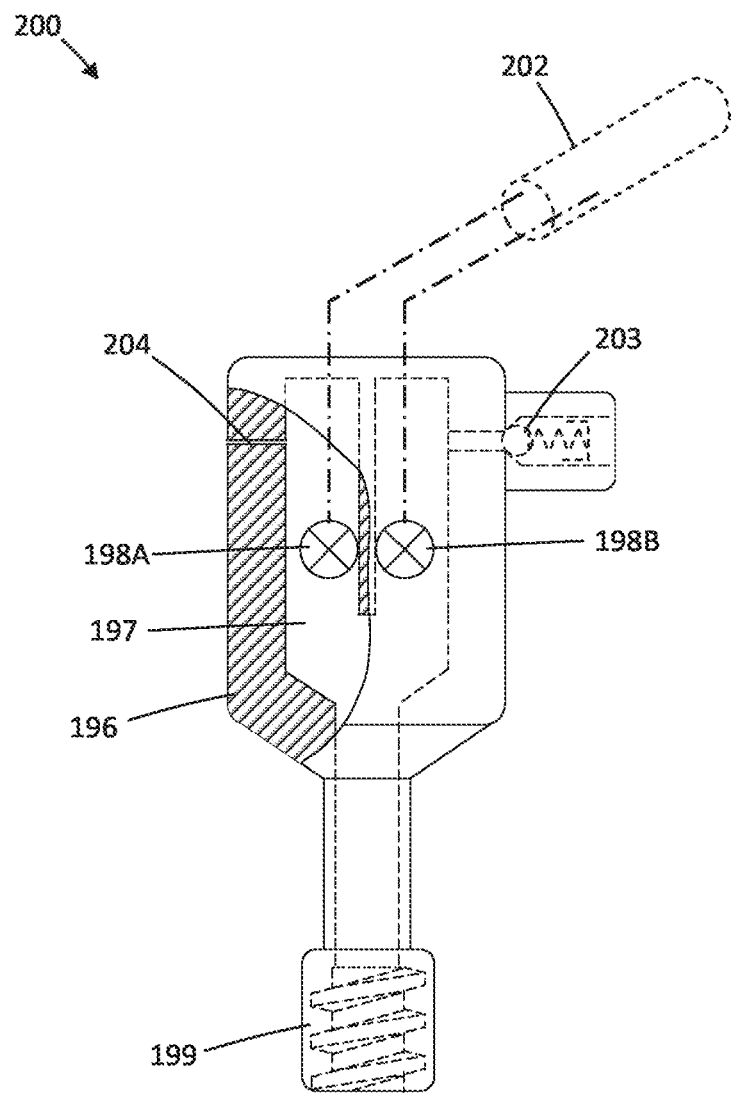
FIG. 7 is an enlarged cut-away view of a pressure sensor as shown in the assembled endoscope of FIGS. 3 and 4.

FIG. 7 is an illustration of one variation of disposable sensor 200 with a body 196 having an interior chamber 197 carrying dual sensor mechanisms 198A and 198B that communicate with controller 25 via cable 202. The pressure sensor mechanism can be any type known in the art. The sensor body 196 has a threaded connector 199 that is adapted to couple to the luer fitting 114b on the endoscope 15 that communicates with fluid channel 112b. In operation, a control algorithm can compare the readings from the two sensor mechanisms 198A and 198B to insure accuracy in sensing pressure and can signal the physician, or disable the system, if there is a discrepancy in pressure readings from the two sensors which would indicate a sensor failure. In FIG. 7, the sensor further shows an optional pressure relief valve 203 in the sensor body. The sensor variation of FIG. 7 further depicts an air purging channel 204 having a very small dimension that extends from the interior chamber 197 to an exterior of the sensor body 196. The air purging channel 204 can have a cross-section of between 0.0001" and 0.001" for releasing air therethrough. In use, the air purging channel 204 will quickly release air from the system to purge the sensor 200 and channel 112b but the small dimension of the channel 204 will prevent any appreciable amount of distention fluid from leaking through the channel.

FIG. 3 schematically illustrates the fluid management system 10 in operation in a diagnostic procedure. The uterine cavity 175 is a potential space and needs to be distended to allow for hysteroscopic viewing. A selected pressure can be set in the controller 25, for example via a touch screen 205, which the physician knows from experience is suited for distending the cavity 175 and/or for performing the diagnostic procedure. In one variation, the selected pressure can be any pressure between 0 and 150 mm Hg. In one system variation, the first peristaltic pump 40A is operated by the controller 25 to operate as a variable speed positive displacement pump that is actuated on demand to provide a flow rate from zero up to 1000 ml/min through inflow line 45. In one variation, the second peristaltic pump 40B operates at a fixed speed to move the saline distention fluid from the uterine cavity 175 through the outflow line 50. In use, the controller 25 and a control algorithm can operate the pumps 40A and 40B at selected matching or non-matching speeds to increase, decrease or maintain the volume of saline distention fluid 12 in the uterine cavity 175. Thus, by independent control of the pumping rates of the first and second positive displacement pumps 40A and 40B, a selected set pressure in the body cavity can be achieved and maintained in response to signals of actual intra-cavity pressure provided by pressure sensor 200.

Figure 6:
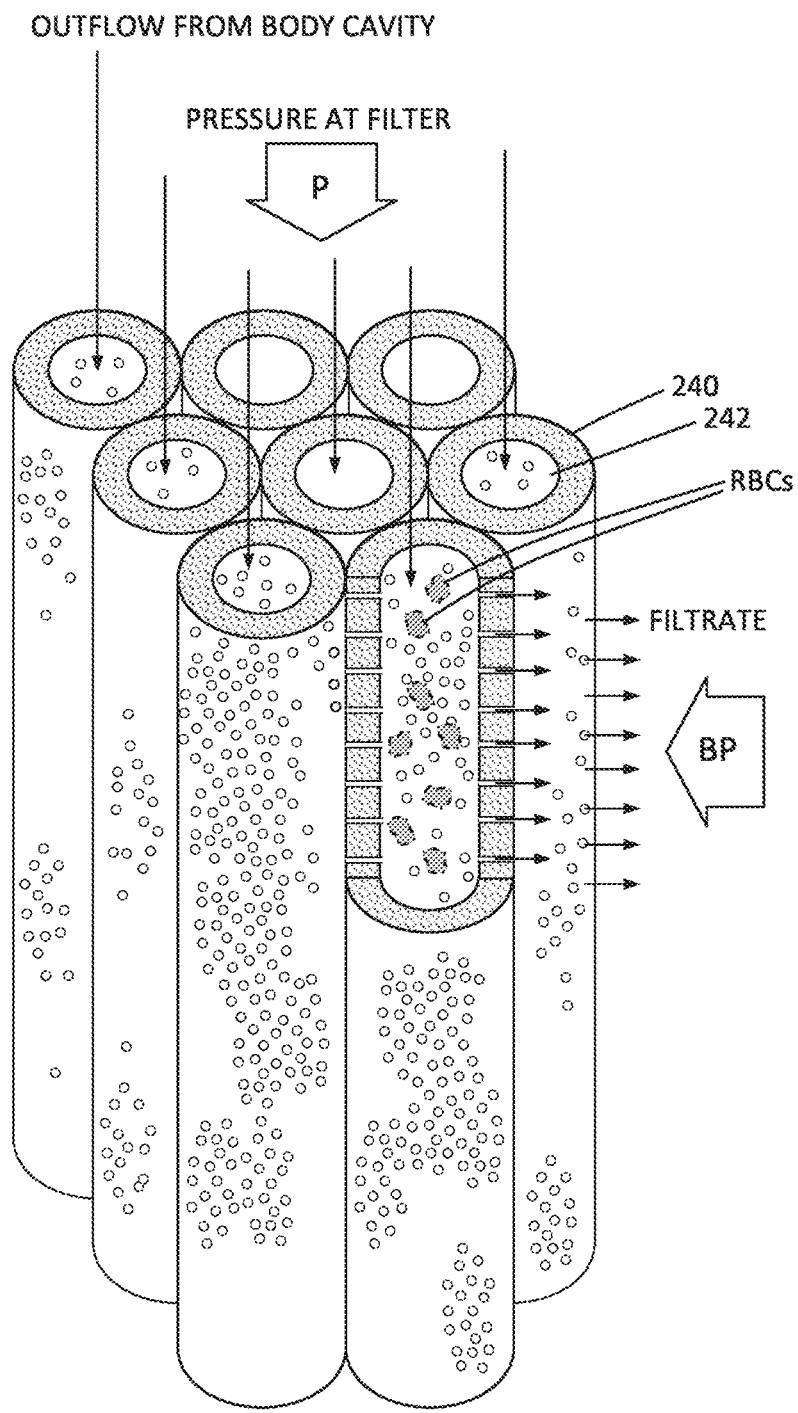
FIG. 6 is a schematic view of hollow fibers of a filter of FIG. 5.

More in detail, a system variation is shown schematically in FIG. 5 which includes a filter module or subsystem 180 that includes a first filter or tissue-capturing filter 210 that is adapted to catch tissue chips 165 that have been resected and extracted from the uterine cavity 175. A second filter or molecular filter 55, typically a hollow fiber filter, is provided beyond the first filter 210, wherein the molecular filter 55 is adapted to remove blood and other materials from the distention fluid 12. In particular, the molecular filter 55 is capable of removing red blood cells, hemoglobin, proteins, bacteria, viruses and the like from the distention fluid 12. FIG. 6 is a cut-away schematic view of a few hollow fibers 240 of a molecular filter 55 illustrating the saline outflow carrying red blood cells (RBC) into the lumens 242 of the hollow fibers where such RBCs are filtered or captured. FIG. 6 further shows a fluid pressure P at the filter interface and a backpressure BP on the filter that comprise filter characteristics that are further discussed below. The filter 55 includes filter characteristics that remove RBCs, albumin and other proteins which insure that endoscopic viewing of the uterine cavity is not obscured or clouded by any blood components or other contaminants. Hollow fiber membrane filters are known in the art, and can be fabricated by manufacturers of filters for ultrafiltration, dialysis and water filtration systems.

As can be understood from FIGS. 3 and 5, the second peristaltic pump 40B at its outflow side 190 provides a positive pressure relative to fluid flows into the filter module 180 to move the distention fluid 12 and tissue media through the first and second filters, 210 and 55, and in a re-circulating flow back to the fluid source 60.

Referring to FIG. 5, in an embodiment, the first filter 210 comprises a container portion or vial 220 with a removable cap 222. The inflow of distention fluid 12 and body media flows though outflow line portion 195 and through an inlet fitting and then into a mesh sac or perforate structure 228 disposed in the interior chamber 230 of the vial 220. The pore size of the perforate structure 228 can range from about 200 microns to 10 microns. The lumen diameter of hollow fibers 240 in the second filter 55 can be from about 400 microns down to 20 microns. In general, the pore size of perforate structure 228 in the first filter 210 is less than the diameter of the lumens 242 of hollow fibers 240 in the second filter 55. In one embodiment, the pore size of the perforate structure 228 is 100 microns, and the lumen size of the hollow fibers 240 in the molecular filter 55 is 200 microns. In one embodiment, the first filter 210 can have a capacity of holding at least 50 grams or at least 100 grams of tissue chips.

Referring to FIG. 5, it can be seen that the filter module 180 includes detachable connections between the various fluid outflow lines to allow for rapid coupling and de-coupling of the filters 55 and the flow lines. More in particular, flow line 50 extending from the tissue resecting device 20 has a connector portion 244a that connects to inlet fitting 244b in the first filter 210. Outflow line portion 250 that is intermediate the filters 210 and 55 has connector portion 252a at its inflow end that connects to outlet fitting 252b in first filter 210. That outflow line portion 250 has another connector 254a at its downstream end that connects to inlet fitting 254b of the second filter or molecular filter 55.

The outflow line portion 255 that is intermediate the molecular (second) filter 55 and fluid source 60 has connector portion 262a that connects to outlet fitting 262b in the second filter 55. In one variation, at least one check valve 265 is provided in the flow path intermediate the filters 210 and 55 which for example can be in line 250, in the connectors 252a or 254a or in the fittings 252b or 254b. In FIG. 5, a check valve 265 is integrated with the inlet end of the molecular (second) filter 55. In use, the operation of the system will result in substantial fluid pressures in the interior of the second filter, and the check valve 265 allows for de-coupling the first filter without escape of pressure and release of fluid media into the environment, for example, when the tissue resection procedure is completed and the physician or nurse wishes to transport the via 1220 and tissue chips 165 therein to a different site for biopsy purposes. In other embodiments, a check valve can be provided in either or both fittings 244b and 252b of the tissue catch filter 210.

In one aspect, a fluid management system comprising a first fluid line 45 configured to carry distention fluid 12 or influent from fluid source 60 to a uterine cavity 175, a second fluid line 50 is configured to carry fluid from the body space to a first filter 210 and then to a second molecular filter 55 and then back to the fluid source 60, a pump 40B operatively coupled to the second fluid line 50 to move the fluid and at least one check valve 265 in the second outflow fluid line intermediate the first and second filters 210 and 55.

In one variation, the fluid management system includes a one-way float valve 285 in the inflow line 45 proximate the spike 288 that is inserted through port 290 in a saline sac comprising the saline source 60. The float valve 285 closes the inflow line when the saline source 60 is empty to prevent air from entering the inflow line 45. A similar float valve (not shown) can be provided in outflow line 50 between the second pump 40B and the filter module 180.

FIG. 4 schematically illustrates the fluid management system 10 in operation as in a myomectomy procedure. As can be seen in FIG. 4, the tissue resecting device 20 of FIG. 1 has been introduced through the working channel 106 of the endoscope 15 into the uterine cavity. The outflow tubing portion 50 is coupled to the quick-connect fitting 170 of the resecting device 20 and thus the fluid pathway for outflows is through the extraction channel 166 of the resecting device 20 (see FIG. 1). In all other aspects, the fluid management system 10 functions in a similar manner as described above.

In one embodiment, the controller 25 of the fluid management system 10 has a screen 205 that is configured to display the volume of fluid remaining in the source 60. In a variation described further below, a control algorithm calculates and displays a fluid deficit which is measured as a difference between a fluid volume delivered to a uterine cavity 175 and a fluid volume recovered from the cavity during a procedure such as fibroid removal (see FIG. 4). A method of fluid management in a hysteroscopic procedure comprises providing a distention fluid source 60 (FIG. 4) having a predetermined volume, introducing saline 12 from the source 60 through a first flow path or line 45 into the uterine cavity 175 and through a second outflow line 50 out of the cavity into a filter module 180 and through a further portion 255 of the second outflow line 50 back to the fluid source 60 wherein the interior volume of the first and second flow lines and the filter module when subtracted from the predetermined volume of the source 60 equals 2500 ml or less to thereby insure that maximum saline intravasion is less than 2500 ml. In this variation, the predetermined volume of the source 60 can be 3.0 liters, as in a standard 3 liter saline bag, and the interior system volume can be at least 0.5 liters. In a variation, the fluid management system 10 can include a sensor system for determining the volume of fluid remaining in the source 60, and the sensor can provide a signal to the controller 25 which in turn can provide a visual or aural signal relating to remaining fluid volume in fluid source 60. In one variation, the fluid source 60 can be a saline bag that hangs from a member including a load cell 280 (FIGS. 3-5) which is configured to send load signals over cable 282 to the controller 25. The controller screen 205 can continuously display a fluid parameter such as fluid remaining in the fluid source 60 based on signals from load cell 280. In other variations, the sensor adapted for sensing the weight or volume of fluid in the fluid source can be a float or level sensor in a fluid source 60, an impedance or capacitance sensor coupled to the fluid source, an optical sensor operatively coupled to the fluid container or any other suitable type of weight or volume sensing mechanism.

In another aspect of the invention, the control algorithm is adapted to display a fluid deficit on the controller screen 205, instead of fluid volume remaining in the source 60. The display of such a fluid deficit can reflect fluid intravasation. In order to accurately calculate such a fluid deficit with the fluid management system 10, it is necessary to account for the fluid capacity within the filter module 180 and the tubing sets, which can be termed dead volume, which is approximately 0.5 liters in one embodiment. It can be understood that the filter module 180 and inflow and outflow tubing lines 45 and 50 are shipped sterile and are filled with air. One means for accounting for the system dead volume is to purge the system and then use a reference weight/volume of the saline sac 60 after its volume has been reduced by the dead volume of the system. There are several means of purging air from the system with distention fluid. FIG. 7 illustrates a method of purging the fluid management system at the time the system is set up in preparation for use in a diagnostic or therapeutic procedure. In this method, a purge adapter 295 with fittings 296a and 296b is connected between the free ends of the inflow line 45 and outflow line 50. Thereafter, a control algorithm operates the controller 25 to actuate the pumps 40A and 40B to pump saline through lines 45 and 50 and filters 210 and 55 back to the saline source 60 which purges air from the system. The control algorithm can operate the pumps and monitor flow volume via pump speed to determine the correct amount of flow required to fill the system with saline, which can be approximately 500 ml. After the purge cycle is complete, the control algorithm then records a pre-procedure reference weight from the load cell 280 and calculates a reference volume of saline in the source 60. Thereafter, during a procedure, the control algorithm can continuously or intermittently display the change in volume (calculated from the measured weight as determined by load cell 280) remaining in source 60 which will reflect fluid loss during the procedure. Such fluid loss can be assumed to be intravasation into the patient, but other losses are possible such as leakage from the cervix or fluid loss during insertion and withdrawal of the hysteroscope or a resecting device. In a variation of a control algorithm, the outflow pump 40B can be controlled to always operate at a higher speed that the inflow pump 40A to insure that the filter module 180 and inflow and outflow lines 45 and 50 are not over-pressurized. An over-pressure condition could arise from kinked tubing, for example.

In another variation and purging method, the pressure sensor 200 (before connecting to endoscope 15 as in FIG. 3) is coupled to the purge adapter 295 of FIG. 7 to monitor pressure within the system during the purge cycle. The pressure sensor 200 then can send signals to the controller 25 wherein a control algorithm controls the pumps 40A and 40B to maintain a predetermined pressure during the purge cycle or operate the pumps to prevent any pressure over a predetermined maximum pressure.

Figure 8:
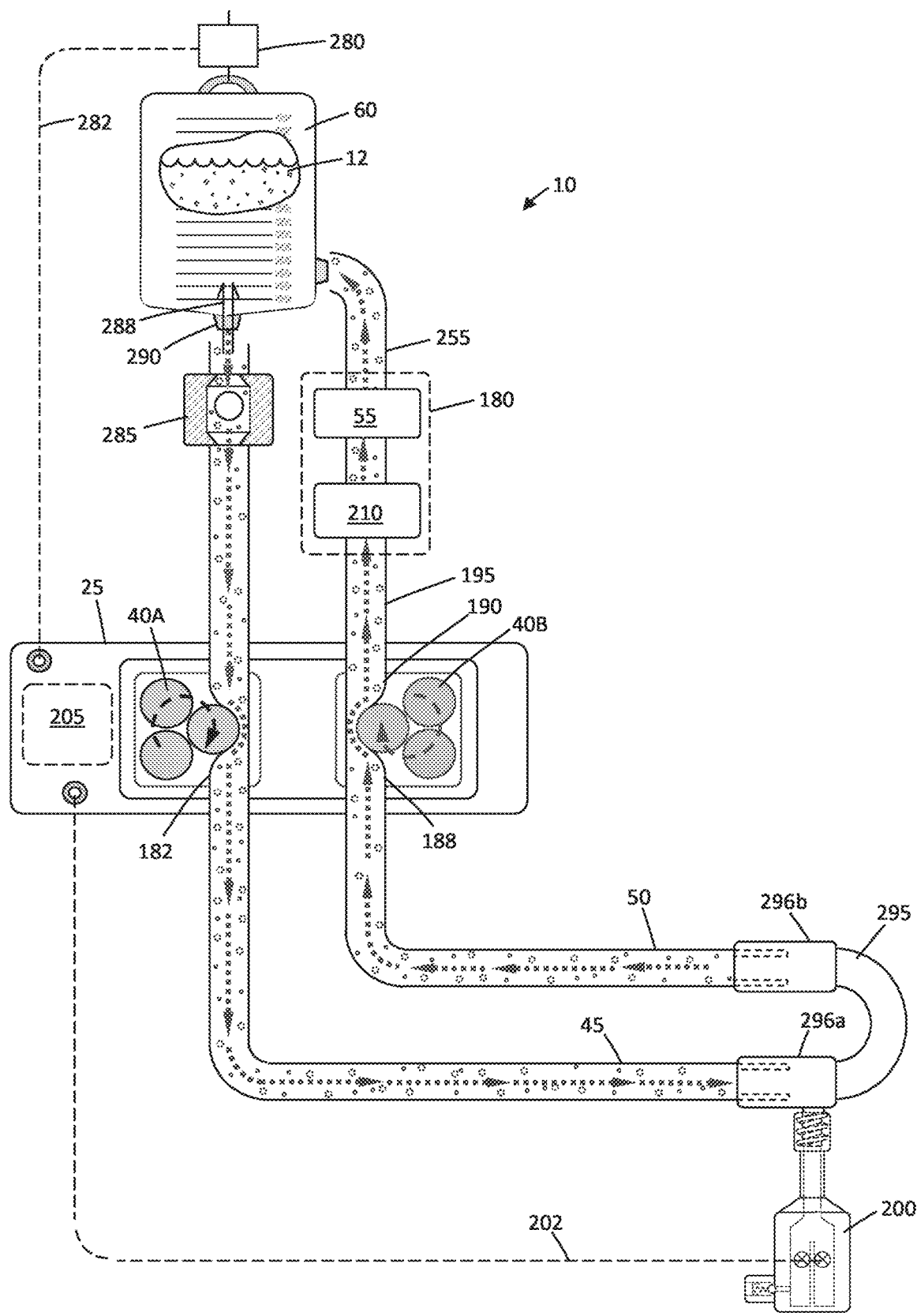
FIG. 8 is a schematic view of the fluid management system of FIGS. 3 and 4 together with a purge adapter illustrating a method of purging the tubing set and filter module.
Figure 9:
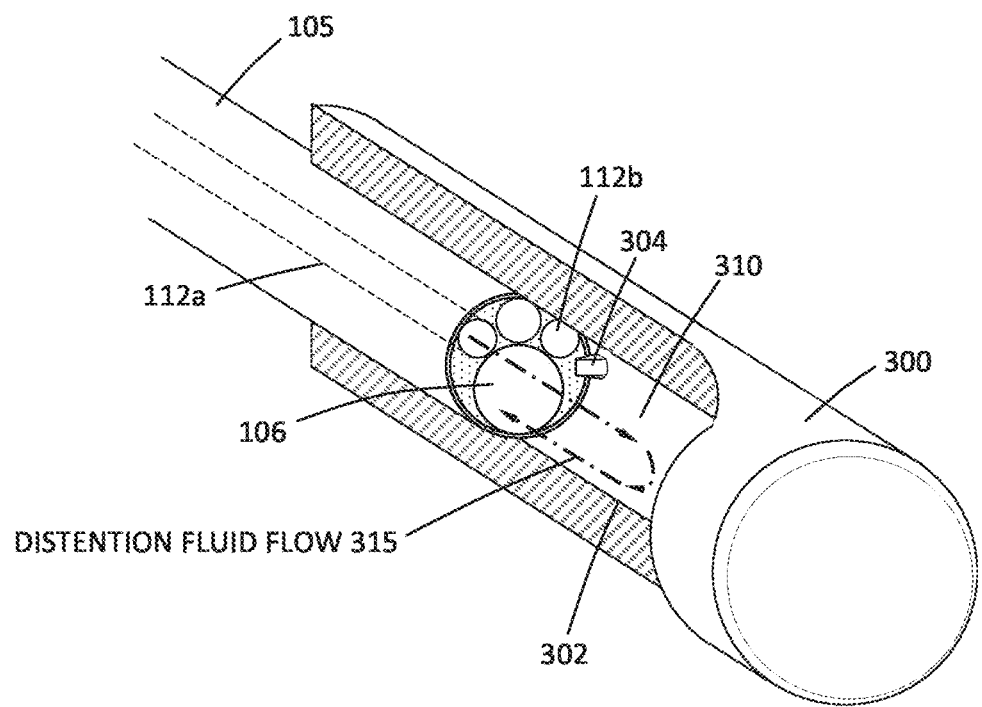
FIG. 9 is a cut-away view of a cap for the distal end of the endoscope of FIGS. 1, 3 and 4 together illustrating another method of purging the tubing set and filter module.

In another method of purging the system, the system can be assembled as depicted in FIGS. 3 and 9, with a disposable cap 300 placed over the distal end of the endoscope shaft 105. The cap 300 can be made of an elastomeric material or a hard plastic having a bore 302 that fits closely over the endoscope shaft 105. The bore 302 optionally can have an o-ring for providing a substantially fluid-tight seal over the endoscope shaft 105. The cap 300 is configured with a stop element 304 to limit the insertion depth of the endoscope shaft 105 to thus provide a chamber 310 through which fluid can circulate. As can be easily understood from FIGS. 3 and 9, a method of purging the system is similar to that of FIG. 8. In FIG. 9, the pumps 40A and 40B can be activated and fluid will flow through channel 112a into chamber 310 (FIG. 9) and then outward through working channel 106 to the outflow line 50 and filter module 180 back to fluid source 60. The circulating flow of distention fluid is indicated at 315 in FIG. 9. As can be understood from FIGS. 3 and 9, the sensor channel 112b is exposed to chamber 310 in cap 300 to thus allow the controller 25 to receive pressure signals of the pressure in chamber 310 during the purge cycle. As described above, a control algorithm then can control maximum pressure during the purge cycle which can be used to prevent over-pressurization of the inflow and outflow lines and filter module 180 which could occur because of kinked tubing.

Another method of purging the air from the system is to assemble the inflow and outflow lines, 45 and 50, with the endoscope 15 as shown in FIG. 3. In this variation, the endoscope would be left in the open in the operating room, and the inflow pump 40A would be activated by a control algorithm to purge the inflow line 45 and endoscope channel 112a with distention fluid which would then exit the endoscope 15 into a waste container. At the same time, the outflow pump 40B would be activated in a reverse direction which would pull fluid from source 60 backwards through the filter module 180 and then through the endoscope 15 and into the waste container. By this method, air would be purged from the tubing set and filter module 180 and an accurate pre-procedure reference volume in source 60 could be recorded to allow accurate deficit monitoring. In this variation, the filter module 180 and outflow line 50 would be provided without check valves to allow reverse flow through the system.

In any variation of the system described above, the controller 25 can provide fluid deficit calculations and fluid intravasation warnings. In another variation, the controller 25 can have an interface and algorithms that allow the physician to set a particular fluid deficit level, (e.g., 1 liter, 1.5 liters, 2 liters, etc.) and an alarm can be signaled when the selected deficit level is reached. In another variation, the fluid deficit control algorithm can include an interlock that disables the fluid management system 10 and/or the resecting device 20 when a selected deficit level is reached.

Now turning to more particular requirements of the filter module 180, the molecular filter 55 has specific filter characteristics and the control algorithms are adapted to provide controlled flows through the filter 55, all of which are required for diagnostic and/or therapeutic use. In one variation, a requirement is that the system and filter 55 have capacities suitable for hysteroscopic procedures such as a myomectomy. For a myomectomy, the authors designed and tested different control algorithms and different flow parameters to determine the optimal range of flow rates that could provide rapid uterine cavity distention, rapid increases in intra-cavity pressure as a tamponade, rapid increases in flow rates to flush the cavity to improve visualization and that could provide suitable flow rates through a resecting device to transport resected tissue chips 165 through the outflow channel line to the tissue collection filter 210. It was determined that controlled flow rates up to a maximum of 1,000 ml/min could be used, and the controller 25 would include control algorithms to operate pumps 40A and 40B independently to provide inflow rates and outflow rates from zero to 1,000 ml/min. The pumps and inflow and outflow rates can be controlled in response to signals from pressure sensor 200 to thereby allow distention of the uterine cavity 175 and maintenance of a set pressure in the uterine cavity.

A corresponding requirement is that the filter 55 have a capacity for flows through the filter membrane at up to at least 500 ml/min, and in another variation 1,000 ml/min, which in turn required the design and development of test protocols for determining the required surface areas of the filter membrane, the pore size or nominal molecular weight limit (NMWL) of the filter, the pressure at the filter interface and pressure gradient across the filter membrane as well as blood volume that would need to be filtered in a myomectomy procedure including a safety factor. The term pressure gradient as used herein describes the fluid pressure at the filter interface less the backpressure BP on the filter 55 (see FIG. 6). In one variation, a hollow fiber membrane filter was used and the pore size or NMWL (discussed further below) was selected to filter at least red blood cells (RBCs). In one variation, the hollow fibers have a nominal molecular weight limit of 50 kDa or less which will filter red blood cells and cell components from the fluid flows. In another variation, the molecular filter 55 is configured with hollow fibers having a nominal molecular weight limit of 20 kDa or less, for example a NMWL of 15 kDa, which in addition to filtering RBCs can remove viruses, coagulation related factors, cytokines and the like as will be described further below.

In order to specify the filter surface area, and thus capacity, of the molecular filter 55 for a myomectomy procedure, the authors determined a value for expected blood loss in a myomectomy procedure. In various studies, the average blood loss in a myomectomy has been determined and in the following two studies, it was found that blood loss was 33.4 ml and 40.1 ml, respectively. (Phillips D. R., Nathanson H., Milim S. J., Haselkom J. S. (1996), "The Effect of Dilute Vasopressin Solution on Blood Loss During_Operative Hysteroscopy", *The Journal of the American Association of Gynecologic Laparoscopists*, 3 (4, Supplement), S38; and Liu M. B., He Y. L., Zong L. L., Yang F. (2004). "Clinical Application of Hysteroscopic Electroresection in 775 cases", *Di Yi fun Yi Da Xue Baa (Academic Journal of the First Medical College of PLA)*, 24 (4), 467-9).

On the basis of the selected flow rates described above and the anticipated blood loss (described above) in a myomectomy procedure, testing resulted in the determination that the molecular filter 55 (or filters) required a membrane surface area of at least 0.5 m², wherein the membrane surface area is defined as the total surface area of the lumens 242 of the hollow fibers 240 (FIG. 6) in the molecular filter 55 (or filters). In another aspect of the invention, the filter characteristics are selected to provide the capacity of filtering at least 40 ml of blood from flow of distension fluid in an operative hysteroscopy.

In other variations, the filter 55 has larger filtering capacity with a membrane surface area of at least 1.0 m² and 1.5 m².

In another aspect of the invention, it was determined that the molecular filter 55 and flow parameters would be designed and selected to prevent any change in the electrolyte concentration of the saline filtrate. In any variation described above, the molecular filter 55 has a nominal molecular weight limit that is greater than the molecular weight of salt (in the range of 26 D) so that salt passes through the filter membrane. A potential source of media that could alter the electrolyte concentration of the distension fluid would be lysed red blood cells (hemolysis) which would release intracellular electrolytes such as calcium, potassium, magnesium, sodium, phosphate and chlorine that could affect the filtrate's electrolyte concentration. Since the intracellular concentrations of these electrolytes are higher than the electrolyte concentration of the saline distension fluid, the lysing of large quantities of red blood cells could result in elevated levels of electrolytes in the re-circulating saline. Intravasation of such saline with the higher electrolyte concentrations could thus result in hypercalcemia, hyperkalemia, hypermagnesemia, hypematremia, hyperphosphatemia or hyperchloremia. Any such electrolyte imbalance over time could negatively affect vital body systems and result in kidney failure and other serious disorders of the heart, brain or muscles.

The authors determined that several factors are relevant in causing and/or preventing hemolysis, which would thus alter electrolyte concentrations of the saline, including the fluid pressure P (see FIG. 6) at the interface of the molecular filter, the flow rate of fluid into and through the filter 55 which is dependent on filter surface area and the nominal molecular weight limit of the hollow fibers. If the pressure or rapid changes in flow are too high, such factors could rupture the walls of red blood cells (RBCs). Further, if the NMLW of the filter is too large, the RBCs could be partially captured in the membrane and turbulence could rupture the cell membranes. Thus, the system design required testing, design, development and selection of filter characteristics and controlled flow parameters that would prevent such hemolysis. In one variation, it was found that RBCs would not be lysed with a filter membrane of at least 0.5 m², a controlled maximum pressure at the filter of 50 psi with a selected maximum flow rate of up to 1,000 ml/min, the selected NMLW parameters described above (e.g., 20 kDa or less) and the anticipated blood loss volumes of at least 40 ml. as described above. In order to insure that the change in flow and pressure is not excessive, the system controller 25 includes software control algorithms that are responsive to pump motor voltage which corresponds to pump speed which in turn determines flow rates and from which pressure at the filter membrane interface can be calculated corresponding to a look-up table linked to the control algorithm. In this variation, the controller 25 can modulate the operation and speed of the second pump 40B to prevent any pressures above 50 psi at the interface of filter 55. The back pressure on the filter is determined by gravity and the height of the saline source 60 above the filter, which is limited to 3 psi or less. In another variation, the controller 25 can include software control algorithms that are responsive to an optional pressure sensor 292 as shown in FIG. 5 which sends signals of in-line pressure to the controller 25. The controller 25 can then modulate the second pump 40B to prevent any unwanted excessive pressure at the interface with filter 55. In other variations, the controller 25 can modulate second pump 40B to prevent any pressures above 60 psi or to prevent any pressures above 100 psi at the filter membrane. Thus, in an aspect of the invention, the filter characteristics were selected and the software control algorithms were developed to control the outflow rate through the filter 55 and control the pressure at the filter membrane to thus prevent any substantial hemolysis. In another aspect, the filter characteristics and control algorithms were developed to control the flow rates and fluid pressure at the filter to prevent lysing of more than 5% of filtered red blood cells.

It was determined that another requirement was that the molecular filter 55 and flow parameters should not allow for coagulation factors and other proteins related to hemostatic activity to pass through the filtration system. Thus, in one variation, the system could have a 70 kDa (70,000 Da) filter 55 that would remove Prothrombin which is an important coagulation factor and well as larger coagulation factors shown in Table A below. In another variation, the system can have a 50 kDa filter that would remove Albumin which has a molecular weight of 64 kDa as well as larger factors (see Table B below). In a preferred embodiment, the system has a filter with a NMWL of 20 kDa or less, for example 15 kDa, which removes all important coagulation proteins as well as other factors described below. Such important coagulation proteins and their molecular weights are shown in Table A below.

TABLE A

| Number and/or name | Molecular Weight |
|---|---|
| I Fibrinogen | 330,000 |
| II Prothrombin | 72,000 |
| III Tissue Factor | 46,000 |
| V Labile factor | 300,000 |
| VII Stable factor | 50,000 |
| VIII Antihemophilic | 300,000 |
| IX Antihemophilic factor | 56,000 |
| X Stuart-Prower factor | 56,000 |
| XI PTA | 160,000 |
| XII Hageman factor | 76,000 |
| XIII Fibrin stabilizing | 320,000 |

In another aspect of the re-circulating fluid management system 10, the filter 55 with a NMWL of 20 kDa or less which removes all important anticoagulation proteins and other proteins, which are listed below in Table B along with their molecular weights.

TABLE B

| Number and/or name | Molecular Weight (Da) |
|---|---|
| Protein C | 62,000 |
| Protein S | 75,000 |
| Antithrombin III | 58,000 |
| Tumor necrosis factors | 25,000 |
| Albumin | 64,000 |

In another aspect of the re-circulating fluid management system 10, the filter 55 with a NMWL of 15 kDa removes cytokines, such as interleukin-10, tumor necrosis factors and tissue growth factors which are released by the uterus. Table C below is a list of key cytokines and their molecular weights that are filtered out by the 15 kDa molecular filter 55.

TABLE C

| Name Interleukins | Synonym(s) | Molecular Weight (Da) |
|---|---|---|
| IL-1α | Hematopoietin-1 | 30,606 |
| IL-1β | Catabolin | 20,747 |
| IL-1RA | IL-1 receptor antagonist | 20,055 |
| IL-18 | interferon-y inducing factor | 22,326 |
| IL-2 | T cell growth factor | 17,628 |
| IL-4 | BSF-1 | 17,492 |
| IL-7 |  | 20,186 |
| IL-9 | T cell growth factor P40 | 15,909 |
| IL-15 |  | 18,086 |
| IL-3 | multipotential CSF, MCGF | 17,233 |
| IL-5 | BCDF-1 | 15,238 |
| GM-CSF | CSF-2 | 16,295 |
| IL-6 | IFN-β2, BSF-2 | 23,718 |
| IL-11 | AGIF | 21,429 |
| G-CSF | CSF-3 | 21,781 |
| IL-12 | NK cell stimulatory factor | 24,844/37,169 |
| LIF | leukemia inhibitory factor | 22,008 |
| OSM | oncostatin M | 28,484 |
| IL-10 | CSIF | 20,517 |
| IL-20 |  | 20,437 |
| IL-14 | HMW-BCGF | 54,759 |
| IL-16 | LCF | 66,694 |
| IL-17 | CTLA-8 | 17,504 |
| IFN-a |  | 21,781 |
| IFN-β |  | 22,294 |
| IFN-y |  | 19,348 |
| CD154 | CD40L, TRAP | 29,273 |
| LT-β |  | 25,390 |
| TNF-a | Cachectin | 25,644 |
| TNF-β | LT-a | 22,297 |
| 4-IBBL |  | 26,624 |
| APRIL | TALL-2 | 27,433 |
| CD70 | CD27L | 21,146 |
| CD153 | CD30L | 26,017 |
| CD178 | FasL | 31,485 |
| GITRL |  | 20,307 |
| LIGHT |  | 26,351 |
| OX40L |  | 21,050 |
| TALL-1 |  | 31,222 |
| TRAIL | Apo2L | 32,509 |
| TWEAK | Apo3L | 27,216 |
| TRANCE | OPGL | 35,478 |
| TGF-β1 | TGF-β | 44,341 |
| TGF-β2 |  | 47,747 |
| TGF-β3 |  | 47,328 |
| Misc. hematopoietins |  |  |
| Epo | Erythropoietin | 21,306 |
| Tpo | MGDF | 37,822 |
| Flt-3L |  | 26,416 |
| SCF | stem cell factor, c-kit ligand | 30,898 |
| M-CSF | CSF-1 | 60,119 |
| MSP | Macrophage stimulating factor, MST-1 | 80,379 |

In one variation, the authors selected filter characteristics including hollow fibers with NMWL of less than 20 kDa, a membrane surface area of at least 0.5 m² and maximum flow rates of at least 500 ml/min. With these selected characteristics and operating parameters, the authors evaluated the filtration of coagulation factors utilizing a Prothrombin Time assay (PT) which is an in-vitro test that measures the effect of a test material or substance (i.e., filtrate) on the extrinsic coagulation system in human blood. Prothrombin is a protein produced by the liver and is involved in clotting of human blood. During the coagulation cascade, Prothrombin is converted to thrombin, factors V, VII, and X. The PT assay measures the time required to generate fibrin polymers via the extrinsic pathway. Such a PT assay can be performed by a contract research organization, e.g., Toxikon Corporation, 15 Wiggins Avenue, Bedford, Mass. 01730. Using the test parameters described above, the PT assay verified that the filtrate did not cause an effect on the extrinsic coagulation pathway.

In another aspect of the method relating to coagulation factors, the authors used an Unactivated Partial Thromboplastin Time assay (UPPT) to further test the filtrate. A UPPT assay measures the effect of a filtrate on the clotting time of human plasma. More particularly, the UPTT assay measures plasma factors involved in the generation of plasma thromboplastin and measures the time required to generate thrombin and fibrin polymers via the intrinsic pathway. It was found that the filtrate did not cause any effect on the intrinsic coagulation pathway using the selected characteristics and operating parameters described above as verified by the UPPT assay. The UPPT assay, as well as other tests described below, can be performed by a contract research organization such as Toxikon Corporation, 15 Wiggins Avenue, Bedford, Mass. 01730.

In another aspect of the invention, in order to determine that the filtrate was not capable of inducing an inflammatory response in a patient, the authors used a Complement Activation assay to evaluate the filtrate after fibroid resection and the filtration of 64 ml of human blood using the selected filter characteristics and controlled flow parameters described above. The Complement Assay is designed to measure complement activation in human plasma as a result of exposure to an article, in this case the filtrate. The measure of complement activation indicates whether exposure to the filtrate may result in a complement-induced inflammatory immune response. The assay measures the quantity of protein complements C3a and C5b in human plasma that has been exposed to the filtrate. It was found that the filtrate caused no unwanted effect based on the fact that there was no statistically significant difference between either C3a or C5b concentrations in plasma exposed to the filtrate and that of plasma exposed to controls.

In another aspect of the invention, in order to determine that the filtrate would not affect platelet aggregation following fluid recirculation, the authors used a Platelet Aggregation assay to evaluate the filtrate after fibroid resection and the filtration of 64 ml of human blood using the above-described filter characteristics and controlled flow parameters. It was found that the filtrate caused no statistically significant difference in the effect in human platelet spontaneous activation or human platelet ADP-induced aggregation in plasma exposed to the filtrate and that of plasma exposed to controls.

Figure 10:
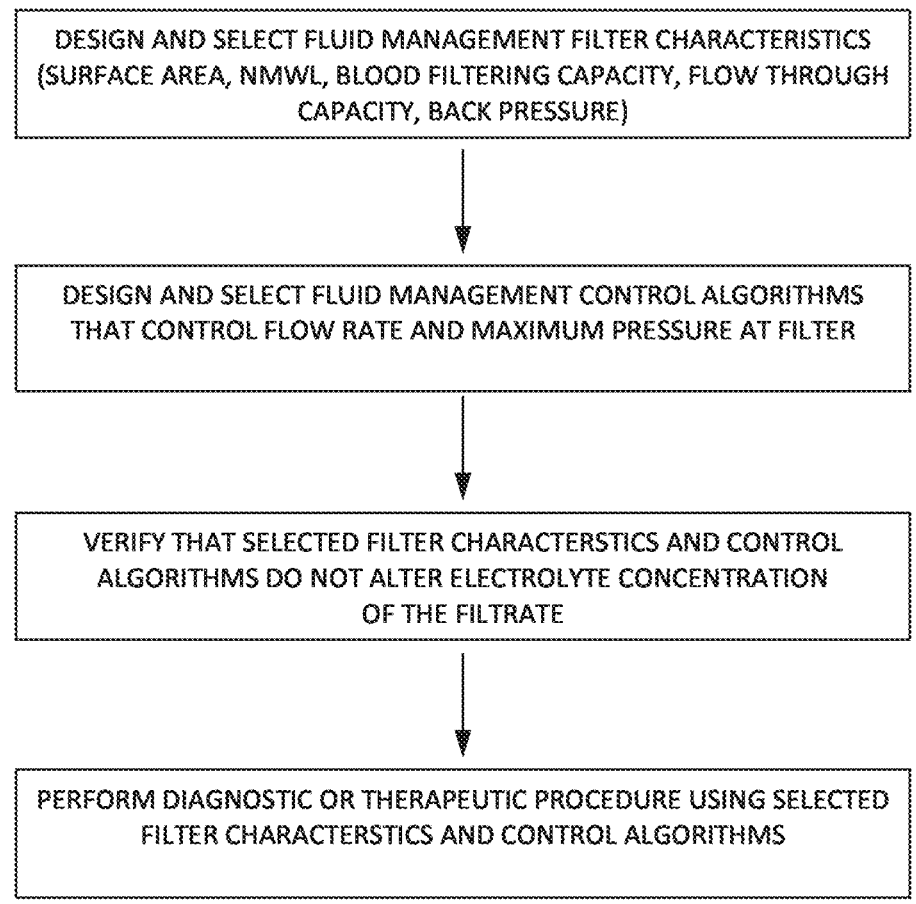
FIG. 10 is a block diagram depicting a method corresponding to the invention relating to selecting filter characteristics and operating parameters and verifying that the filter does not change the electrolyte concentration of the saline.

Thus, a method of fluid management corresponding to the invention as described above comprises providing a re-circulating fluid management system including a saline source, a pump system for providing fluid inflow and outflows, a controller and control algorithms, and a filter system having selected characteristics for filtering the outflows from a site in a patient's body, wherein the filtrate is returned to the source. FIG. 10 depicts a method wherein the filter characteristics are designed and selected, then control algorithms are designed and selected to control flow rates and pressure at the filter interface, and the selected filter characteristics and maximum pressures resulting from the selected flow rate are then verified by electrolyte testing that the saline concentration before filtration and after filtration is not changed. Thereafter, a diagnostic or therapeutic procedure can be performed using the selected filter characteristics and control algorithms. In one variation, the preselected filter characteristics include hollow fibers with a total lumen surface area of at least 0.5 $m^2$ and a NMWL of less than 20 kDa. Further, the filter has a filtration capacity of at least 40 ml of blood. In other variations, the filter has a filtration capacity of at least 60 ml of blood or at least 80 ml of blood.

Figure 11:
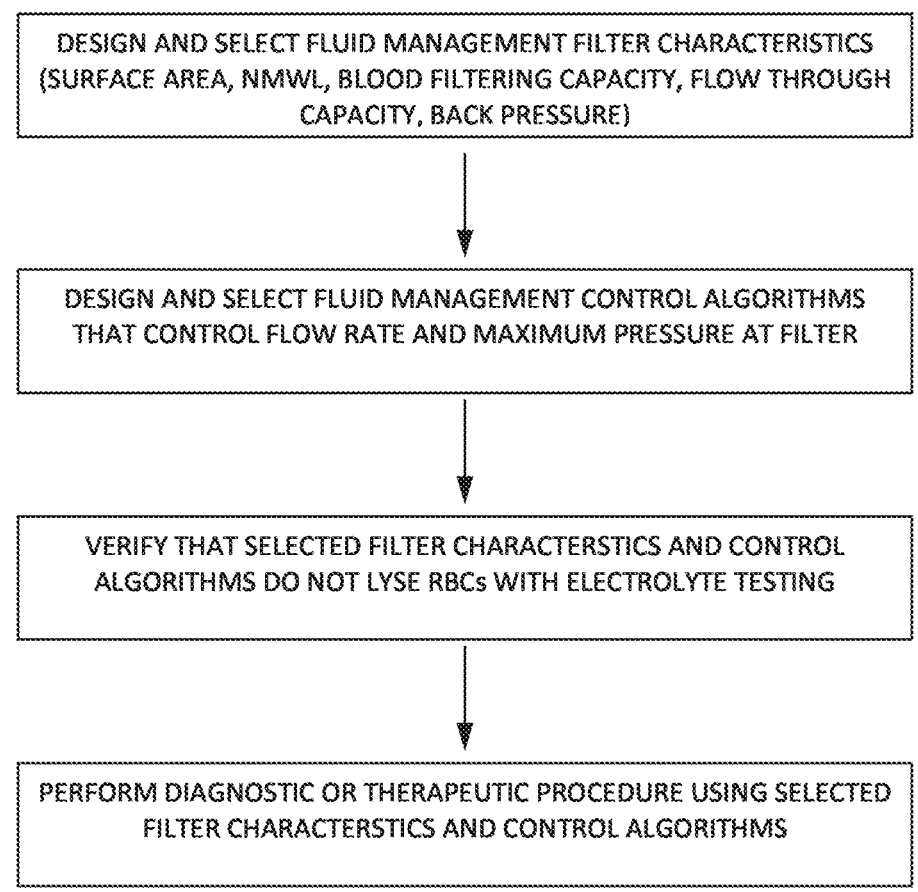
FIG. 11 is a block diagram depicting another method of the invention relating to selecting filter characteristics and operating parameters and verifying that the filter substantially does not lyse red blood cells.

In another aspect, a method of fluid management comprises providing a re-circulating fluid management system including a saline source, a pump system for providing fluid inflow and outflows, a controller and control algorithms, and a filter system having selected characteristics for filtering the outflows from a site in a patient's body, wherein the filtrate is returned to the source. FIG. 11 depicts a method as described above wherein the filter characteristics are designed and selected, then control algorithms are designed and selected to control flow rates and pressure at the filter interface, and the selected filter characteristics and maximum pressures resulting from the selected flow rate are verified to not lyse red blood cells by electrolyte testing. Thereafter, a diagnostic or therapeutic procedure is performed in a treatment site in the presence of the saline. In a variation, the method includes selecting filter characteristics and controlled flow rates that prevent hemolysis greater than 5% of filtered red blood cells.

Figure 12:
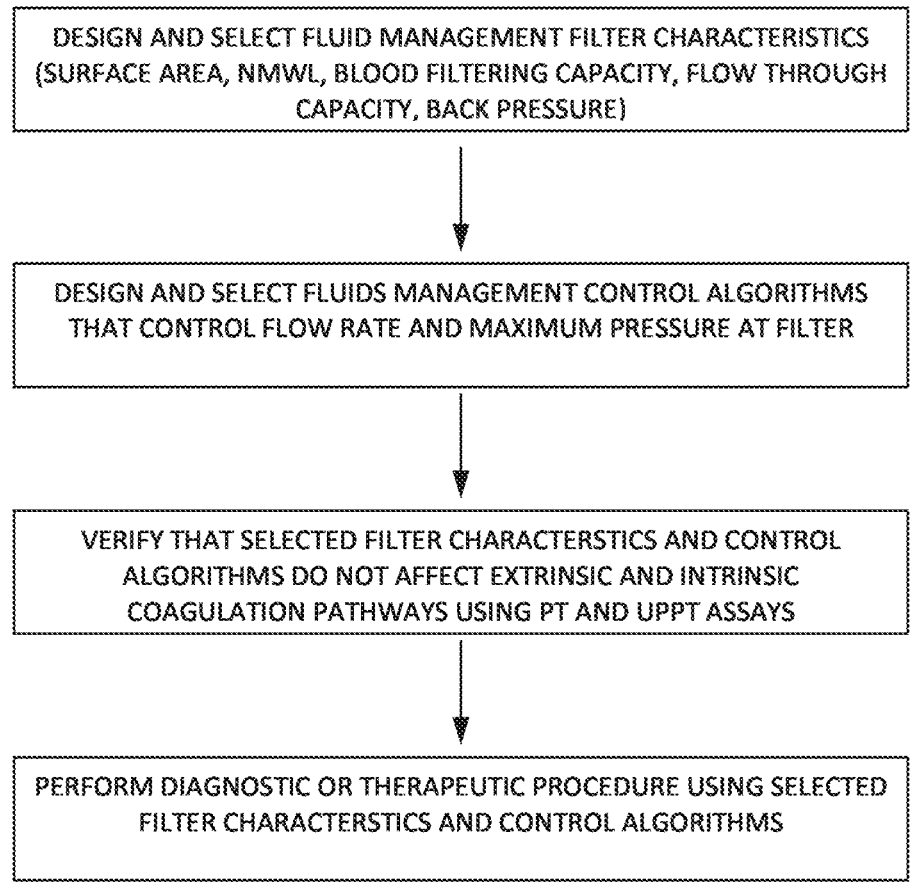
FIG. 12 is a block diagram depicting a method of the invention again relating to selecting filter characteristics and operating parameters and then verifying that the filtrate has no substantial effect extrinsic and intrinsic coagulation pathways as verified by a Prothrombin Time assay and an Unactivated Partial Thromboplastic Time assay.

In another aspect, FIG. 12 depicts a method wherein the filter characteristics are designed and selected, then control algorithms are designed and selected to control flow rates and pressure at the filter interface, and the selected filter characteristics and maximum pressures resulting from the selected flow rate have no substantial effect on an extrinsic coagulation pathway and an intrinsic coagulation pathway as verified by a Prothrombin Time assay and a Unactivated Partial Thromboplastic Time assay.

Figure 13:
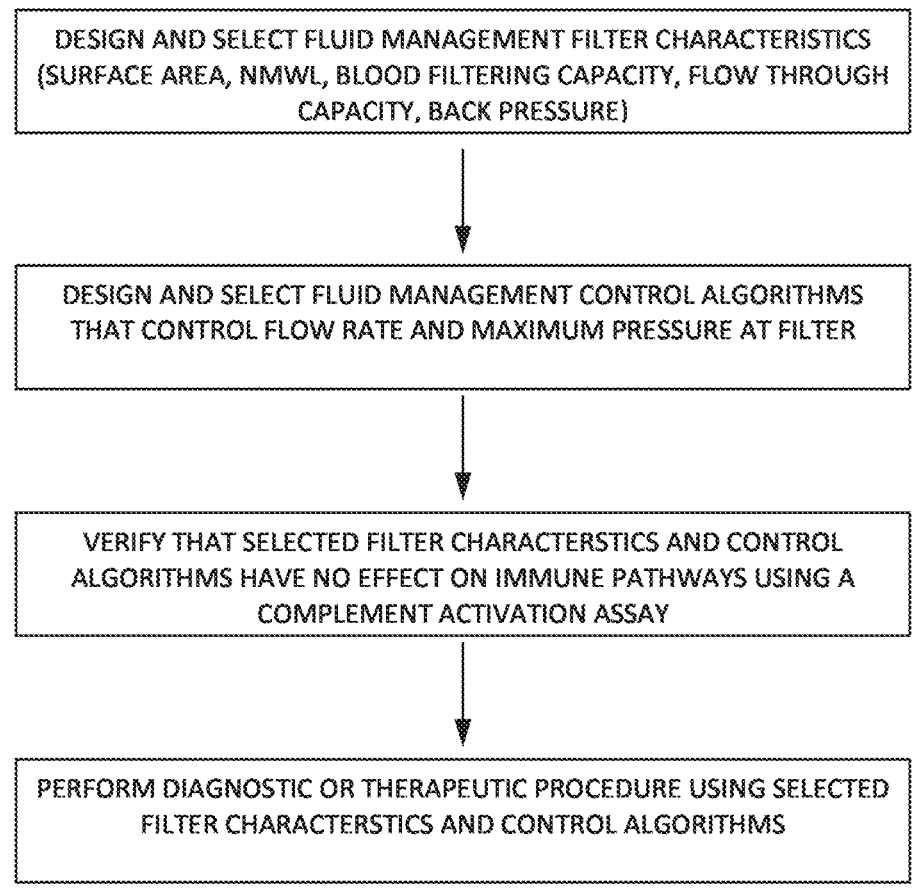
FIG. 13 is a block diagram depicting a method of the invention relating to selecting filter characteristics and operating parameters and then verifying that the filtrate has no substantial effect on an immune system pathway as verified by a Complement Activation assay looking at C3a or C5b concentrations.

In another variation, FIG. 13 depicts a method wherein the filter characteristics are designed and selected, then control algorithms are designed and selected to control flow rates and pressure at the filter interface, and the selected filter characteristics and maximum pressures resulting from the selected flow rate have no substantial effect on an immune system pathway as verified by a Complement Activation assay looking at C3a or C5b concentrations.

Figure 14:
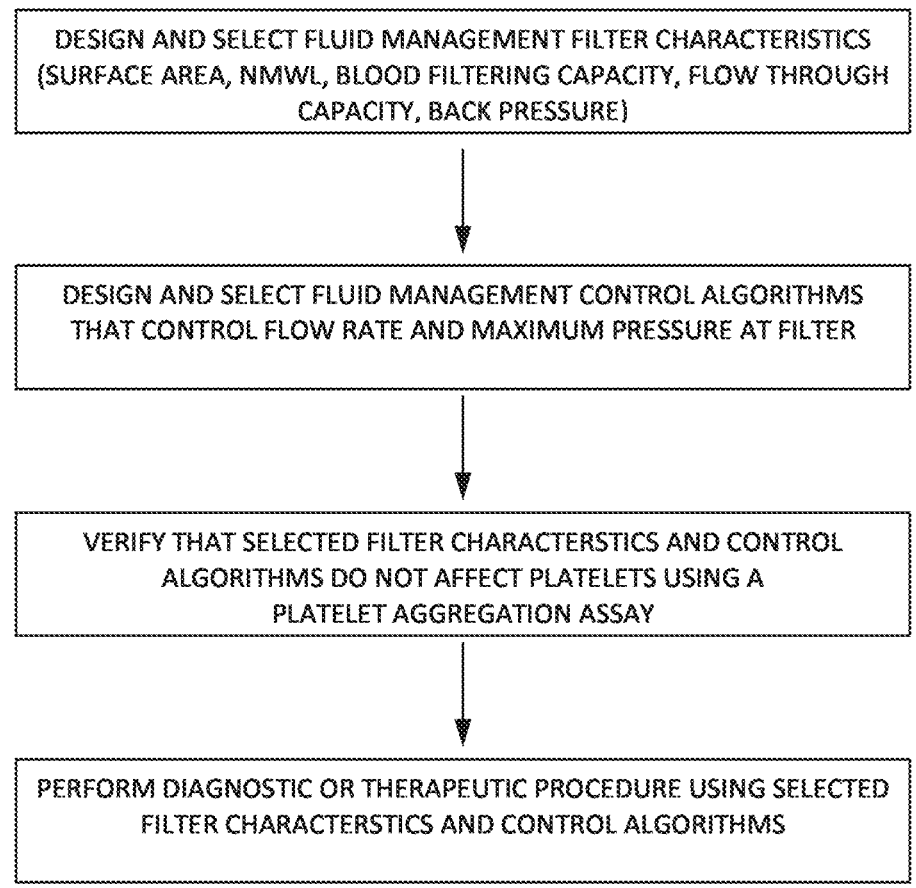
FIG. 14 is a block diagram depicting a method of the invention relating to selecting filter characteristics and operating parameters and then verifying that the filtrate has substantially no effect on platelet activation as verified by a Platelet Aggregation assay.

In another aspect, FIG. 14 depicts a method wherein the filter characteristics are designed and selected, then control algorithms are designed and selected to control flow rates and pressure at the filter interface, and the selected filter characteristics and maximum pressures resulting from the selected flow rate have substantially no effect on platelet activation as verified by a Platelet Aggregation assay.

While certain embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of fluid management during an intrauterine procedure in a uterine cavity of a female patient that causes no substantial effect on an extrinsic or intrinsic coagulation pathway, comprising:
    circulating saline from a saline source in a saline inflow to the uterine cavity and a saline outflow from the uterine cavity through a filter resulting in a flow of filtered saline back to the saline source;
    wherein the circulating step includes filtering red blood cells out of the saline outflow under filtering parameters that provide filtered saline that passes Prothrombin Time and Unactivated Partial Thromboplastic Time assays; and
    performing a diagnostic or therapeutic procedure in the uterine cavity.

2. The method of claim 1, wherein control algorithms control an outflow rate of the saline outflow to thereby limit pressure at the filter to a maximum of 50 psi or less.

3. The method of claim 1, wherein the filter comprises hollow filter fibers with a total lumen surface area of at least 0.5 $m^2$.

4. The method of claim 1, wherein the filter has a filtration capacity of at least 40 ml of blood.

5. The method of claim 1, wherein the filter has a flow-through capacity of at least 500 ml/min.

6. The method of claim 1, wherein the filter comprises hollow filter fibers having a nominal molecular weight limit (NMWL) of 20 kDa or less.

7. The method of claim 1, wherein the filter has a back pressure at the filter of 3 psi or less.

8. The method of claim 1, wherein the filtering parameters are further selected to ensure that the filtered saline passes a Complement Activation assay evaluating at least one of the protein complements C3A and C5b.

9. The method of claim 1, wherein the filtering parameters are further selected to ensure that the filtered saline passes a Platelet Aggregation assay.

10. A method of fluid management during an intrauterine procedure in a uterine cavity of a female patient that causes substantially no activation of an immune system pathway, comprising:
    circulating saline from a saline source in a saline inflow to the uterine cavity and a saline outflow from the uterine cavity through a filter resulting in a flow of filtered saline back to the saline source;
    wherein the circulating step includes filtering red blood cells out of the saline outflow under filtering parameters that provide filtered saline that passes a Complement Activation assay evaluating at least one of the protein complements C3A and C5b; and
    performing a diagnostic or therapeutic procedure in the uterine cavity.

11. The method of claim 10, wherein the filtering parameters are further selected to ensure that the filtered saline passes a Prothrombin Time assay.

12. The method of claim 10, wherein the filtering parameters are further selected to ensure that the filtered saline passes a Platelet Aggregation assay.

13. The method of claim 10, wherein the filtering parameters are further selected to ensure that the filtered saline passes an Unactivated Partial Thromboplastic Time assay.

14. The method of claim 10, wherein the filter has a filtration capacity of at least 40 ml of blood.

15. The method of claim 10, wherein the filter has a filtration capacity of at least 60 ml of blood.

16. The method of claim 10, wherein control algorithms control an outflow rate of the saline outflow to thereby limit pressure at the filter to a maximum of 50 psi or less.

17. The method of claim 10, wherein the filter comprises hollow filter fibers with a total lumen surface area of at least $0.5 \text{ m}^2$.

18. The method of claim 10, wherein the filter has a flow-through capacity of at least 500 ml/min.

19. The method of claim 10, wherein the filter comprises hollow filter fibers having a nominal molecular weight limit (NMWL) of 50 kDa or less.

20. The method of claim 10, wherein the filter comprises hollow filter fibers having a nominal molecular weight limit (NMWL) of 20 kDa or less.

* * * * *